US012357830B2

(12) United States Patent
Dinsmoor et al.

(10) Patent No.: US 12,357,830 B2
(45) Date of Patent: Jul. 15, 2025

(54) SUB-THRESHOLD STIMULATION BASED ON ECAP DETECTION

(71) Applicant: Medtronic, Inc., Minneapolis, MN (US)

(72) Inventors: David A. Dinsmoor, North Oaks, MN (US); Melanie D. Goodman Keiser, Otsego, MN (US)

(73) Assignee: Medtronic, Inc., Minneapolis, MN (US)

( * ) Notice: Subject to any disclaimer, the term of this patent is extended or adjusted under 35 U.S.C. 154(b) by 18 days.

(21) Appl. No.: 17/065,383

(22) Filed: Oct. 7, 2020

(65) Prior Publication Data

US 2021/0121698 A1 Apr. 29, 2021

Related U.S. Application Data

(60) Provisional application No. 62/926,188, filed on Oct. 25, 2019.

(51) Int. Cl.
*A61N 1/36* (2006.01)

(52) U.S. Cl.
CPC ..... *A61N 1/36139* (2013.01); *A61N 1/36153* (2013.01); *A61N 1/36175* (2013.01); *A61N 1/36192* (2013.01)

(58) Field of Classification Search
CPC ............ A61N 1/36139; A61N 1/36153; A61N 1/36175; A61N 1/36192; A61N 1/0531;
(Continued)

(56) References Cited

U.S. PATENT DOCUMENTS

| 5,603,726 A | 2/1997 | Schulman et al. |
| 5,800,465 A | 9/1998 | Thompson et al. |

(Continued)

FOREIGN PATENT DOCUMENTS

| CN | 105031812 A | 11/2015 |
| CN | 105407964 A | 3/2016 |

(Continued)

OTHER PUBLICATIONS

Agnesi et al., "Local Glutamate Release in the Rat Ventral Lateral Thalamus Evoked by High-Frequency Stimulation," Journal of Neural Engineering, vol. 7, No. 2, Apr. 2010, 20 pp.

(Continued)

*Primary Examiner* — James M Kish
*Assistant Examiner* — Natasha Patel
(74) *Attorney, Agent, or Firm* — Shumaker & Sieffert, P.A.

(57) ABSTRACT

Systems, devices, and techniques are described for determining stimulation parameters based on one or more stimulation thresholds (e.g., a perception threshold or a detection threshold). In one example, a medical device includes sensing circuitry configured to sense one or more ECAP signals, wherein the sensing circuitry is configured to sense each ECAP signal of the one or more ECAPs elicited by a respective control pulse of a plurality of control pulses, and the medical device includes processing circuitry configured to determine, based on the one or more ECAP signals, a stimulation level for the plurality of control pulses that achieves a stimulation threshold, determine, based on the stimulation level, a value of a stimulation parameter that at least partially defines a plurality of therapy pulses of electrical stimulation therapy, and control stimulation generation circuitry to deliver the electrical stimulation therapy according to the value of the stimulation parameter.

28 Claims, 11 Drawing Sheets

(58) Field of Classification Search
CPC ............... A61N 1/0534; A61N 1/0551; A61N 1/36062; A61N 1/36064; A61N 1/36067; A61N 1/36071; A61N 1/36107; A61N 1/36132; A61N 1/36146; A61N 1/37235; A61B 5/40

See application file for complete search history.

(56) References Cited

U.S. PATENT DOCUMENTS

| | | | |
|---|---|---|---|
| 6,157,861 | A | 12/2000 | Faltys et al. |
| 6,205,360 | B1 | 3/2001 | Carter |
| 6,289,247 | B1 | 9/2001 | Faltys et al. |
| 6,314,325 | B1 | 11/2001 | Fitz |
| 6,421,566 | B1 | 7/2002 | Holsheimer |
| 6,505,078 | B1 | 1/2003 | King et al. |
| 6,675,046 | B2 | 1/2004 | Holsheimer |
| 6,850,802 | B2 | 2/2005 | Holsheimer |
| 6,988,006 | B2 | 1/2006 | King et al. |
| 7,076,292 | B2 | 7/2006 | Forsberg |
| 7,206,640 | B1 | 4/2007 | Overstreet |
| 7,333,858 | B2 | 2/2008 | Killian et al. |
| 7,450,992 | B1 | 11/2008 | Cameron |
| 7,577,480 | B2 | 8/2009 | Zeijlemaker |
| 7,616,999 | B2 | 11/2009 | Overstreet et al. |
| 7,657,318 | B2 | 2/2010 | King et al. |
| 7,689,289 | B2 | 3/2010 | King |
| 7,742,810 | B2 | 6/2010 | Moffitt et al. |
| 7,792,583 | B2 | 9/2010 | Miesel et al. |
| 8,036,747 | B2 | 10/2011 | Thacker et al. |
| 8,090,446 | B2 | 1/2012 | Fowler et al. |
| 8,504,150 | B2 | 8/2013 | Skelton |
| 8,620,441 | B2 | 12/2013 | Greenberg et al. |
| 8,676,329 | B2 | 3/2014 | Wacnik et al. |
| 8,694,108 | B2 | 4/2014 | Alataris et al. |
| 8,708,934 | B2 | 4/2014 | Skelton et al. |
| 8,712,533 | B2 | 4/2014 | Alataris et al. |
| 8,712,534 | B2 | 4/2014 | Wei |
| 8,751,009 | B2 | 6/2014 | Wacnik |
| 8,897,888 | B2 | 11/2014 | Parker et al. |
| 8,923,984 | B2 | 12/2014 | Parker et al. |
| 9,002,460 | B2 | 4/2015 | Parker |
| 9,072,910 | B2 | 7/2015 | Parker et al. |
| 9,089,714 | B2 | 7/2015 | Robinson |
| 9,089,715 | B2 | 7/2015 | Parker et al. |
| 9,138,582 | B2 | 9/2015 | Doan et al. |
| 9,155,892 | B2 | 10/2015 | Parker et al. |
| 9,283,373 | B2 | 3/2016 | Parker et al. |
| 9,302,112 | B2 | 4/2016 | Bornzin et al. |
| 9,339,655 | B2 | 5/2016 | Carbunaru |
| 9,364,667 | B1 | 6/2016 | Dinsmoor et al. |
| 9,381,356 | B2 | 7/2016 | Parker et al. |
| 9,386,934 | B2 | 7/2016 | Parker et al. |
| 9,387,325 | B1 | 7/2016 | Min et al. |
| 9,566,439 | B2 | 2/2017 | Single et al. |
| 9,597,507 | B2 | 3/2017 | Johanek et al. |
| 9,700,713 | B2 | 7/2017 | Robinson et al. |
| 9,872,990 | B2 | 1/2018 | Parker et al. |
| 9,993,646 | B2 | 6/2018 | Parramon et al. |
| 10,183,168 | B2 | 1/2019 | Baru et al. |
| 10,569,088 | B2 | 2/2020 | Dinsmoor et al. |
| 10,588,524 | B2 | 3/2020 | Single et al. |
| 10,933,242 | B2 | 3/2021 | Torgerson |
| 11,202,912 | B2 | 12/2021 | Dinsmoor et al. |
| 11,524,163 | B2 | 12/2022 | Baynham et al. |
| 11,547,860 | B2 | 1/2023 | Hareland et al. |
| 2004/0267333 | A1 | 12/2004 | Kronberg |
| 2008/0221640 | A1 | 9/2008 | Overstreet et al. |
| 2008/0300655 | A1 | 12/2008 | Cholette |
| 2011/0046432 | A1 | 2/2011 | Simon et al. |
| 2011/0054570 | A1 | 3/2011 | Lane |
| 2011/0071589 | A1 | 3/2011 | Starkebaum et al. |
| 2011/0077712 | A1 | 3/2011 | Killian |
| 2011/0125223 | A1 | 5/2011 | Carbunaru et al. |
| 2012/0155188 | A1 | 6/2012 | Buettner et al. |
| 2012/0226332 | A1* | 9/2012 | Chambers ............ A61N 1/3782 607/57 |
| 2013/0208390 | A1 | 8/2013 | Singh et al. |
| 2013/0268021 | A1 | 10/2013 | Moffitt |
| 2013/0289664 | A1 | 10/2013 | Johanek |
| 2013/0289683 | A1 | 10/2013 | Parker et al. |
| 2014/0005753 | A1 | 1/2014 | Carbunaru |
| 2014/0025146 | A1 | 1/2014 | Alataris et al. |
| 2014/0031896 | A1 | 1/2014 | Alataris et al. |
| 2014/0031905 | A1 | 1/2014 | Irazoqui et al. |
| 2014/0074189 | A1 | 3/2014 | Moffitt |
| 2014/0142656 | A1 | 5/2014 | Alataris et al. |
| 2014/0142673 | A1 | 5/2014 | Alataris et al. |
| 2014/0194772 | A1 | 7/2014 | Single et al. |
| 2014/0236042 | A1 | 8/2014 | Parker et al. |
| 2014/0236257 | A1 | 8/2014 | Parker et al. |
| 2014/0243924 | A1 | 8/2014 | Zhu et al. |
| 2014/0243926 | A1 | 8/2014 | Carcieri et al. |
| 2014/0243931 | A1 | 8/2014 | Parker et al. |
| 2014/0277267 | A1* | 9/2014 | Vansickle .......... A61N 1/36185 607/46 |
| 2014/0277282 | A1* | 9/2014 | Jaax .................... A61N 1/36139 607/59 |
| 2014/0288577 | A1 | 9/2014 | Robinson et al. |
| 2014/0293737 | A1 | 10/2014 | Parker et al. |
| 2014/0296936 | A1 | 10/2014 | Alataris et al. |
| 2014/0324143 | A1 | 10/2014 | Robinson et al. |
| 2014/0371813 | A1 | 12/2014 | King et al. |
| 2014/0378941 | A1 | 12/2014 | Su et al. |
| 2014/0379043 | A1 | 12/2014 | Howard |
| 2015/0005842 | A1 | 1/2015 | Lee et al. |
| 2015/0012068 | A1 | 1/2015 | Bradley et al. |
| 2015/0032181 | A1 | 1/2015 | Baynham et al. |
| 2015/0039057 | A1 | 2/2015 | Della Santina |
| 2015/0057729 | A1 | 2/2015 | Parker et al. |
| 2015/0127062 | A1 | 5/2015 | Holley et al. |
| 2015/0179177 | A1 | 6/2015 | Nagao |
| 2015/0282725 | A1 | 10/2015 | Single |
| 2015/0313487 | A1 | 11/2015 | Single et al. |
| 2015/0360031 | A1 | 12/2015 | Bornzin et al. |
| 2015/0374999 | A1 | 12/2015 | Parker et al. |
| 2016/0082252 | A1 | 3/2016 | Hershey et al. |
| 2016/0121124 | A1 | 5/2016 | Johanek et al. |
| 2016/0129272 | A1 | 5/2016 | Hou et al. |
| 2016/0136420 | A1 | 5/2016 | Brink et al. |
| 2016/0157769 | A1 | 6/2016 | Min et al. |
| 2016/0158550 | A1 | 6/2016 | Hou et al. |
| 2016/0158551 | A1 | 6/2016 | Kent |
| 2016/0166164 | A1 | 6/2016 | Obradovic et al. |
| 2016/0175594 | A1* | 6/2016 | Min .................... A61N 1/36171 607/72 |
| 2016/0206883 | A1 | 7/2016 | Bomzin et al. |
| 2016/0287126 | A1 | 10/2016 | Parker et al. |
| 2016/0287182 | A1 | 10/2016 | Single |
| 2016/0303368 | A1 | 10/2016 | Parramon et al. |
| 2016/0346534 | A1 | 12/2016 | Isaacson et al. |
| 2016/0361542 | A1 | 12/2016 | Kaula et al. |
| 2017/0001017 | A9 | 1/2017 | Parker et al. |
| 2017/0049345 | A1 | 2/2017 | Single |
| 2017/0071490 | A1 | 3/2017 | Parker et al. |
| 2017/0135624 | A1 | 5/2017 | Parker |
| 2017/0173332 | A1 | 6/2017 | Overstreet |
| 2017/0209695 | A1 | 7/2017 | Solomon |
| 2017/0216587 | A1 | 8/2017 | Parker |
| 2017/0216602 | A1 | 8/2017 | Waataja et al. |
| 2017/0296823 | A1 | 10/2017 | Hershey et al. |
| 2017/0361101 | A1 | 12/2017 | Single |
| 2017/0361103 | A1 | 12/2017 | Hadjiyski |
| 2018/0056073 | A1 | 3/2018 | Torgerson |
| 2018/0078769 | A1 | 3/2018 | Dinsmoor et al. |
| 2018/0110987 | A1 | 4/2018 | Parker |
| 2018/0117332 | A1* | 5/2018 | Robinson ............ A61N 1/36139 |
| 2018/0117335 | A1 | 5/2018 | Parker et al. |
| 2018/0126169 | A1* | 5/2018 | Hou .................... A61N 1/37264 |
| 2018/0132760 | A1 | 5/2018 | Parker |
| 2018/0140830 | A1 | 5/2018 | Marnfeldt et al. |
| 2018/0154144 | A1 | 6/2018 | Brink |
| 2018/0200520 | A1 | 7/2018 | Tranchina |
| 2018/0214701 | A1* | 8/2018 | Zhang ................ A61N 1/36132 |

(56) References Cited

U.S. PATENT DOCUMENTS

| | | | |
|---|---|---|---|
| 2018/0256897 A1* | 9/2018 | Parramon | A61N 1/36132 |
| 2019/0099601 A1* | 4/2019 | Torgerson | A61B 5/16 |
| 2019/0105496 A1 | 4/2019 | Min et al. | |
| 2019/0209844 A1 | 7/2019 | Esteller et al. | |
| 2019/0247657 A1* | 8/2019 | Brill | A61N 1/0488 |
| 2019/0388692 A1* | 12/2019 | Dinsmoor | A61N 1/36007 |
| 2019/0388695 A1* | 12/2019 | Dinsmoor | A61B 5/4836 |
| 2020/0038660 A1* | 2/2020 | Torgerson | A61N 1/36164 |
| 2020/0171312 A1 | 6/2020 | Dinsmoor et al. | |
| 2020/0171313 A1 | 6/2020 | Dinsmoor et al. | |
| 2021/0101007 A1 | 4/2021 | Hamner et al. | |
| 2021/0121699 A1 | 4/2021 | Dinsmoor | |
| 2021/0187299 A1 | 6/2021 | Dinsmoor et al. | |
| 2021/0236821 A1* | 8/2021 | Sinclair | A61B 5/4821 |
| 2022/0008731 A1 | 1/2022 | Dinsmoor et al. | |

FOREIGN PATENT DOCUMENTS

| | | | |
|---|---|---|---|
| EP | 2396072 B1 | 3/2013 | |
| EP | 3013413 A1 | 5/2016 | |
| EP | 3024540 B1 | 10/2018 | |
| WO | 2002009808 A1 | 2/2002 | |
| WO | 2010058178 A1 | 5/2010 | |
| WO | 2012155188 A1 | 11/2012 | |
| WO | 2014138990 A1 | 9/2014 | |
| WO | 2014/210373 A1 | 12/2014 | |
| WO | 2015143509 A1 | 10/2015 | |
| WO | 2015179177 A1 | 11/2015 | |
| WO | 2015179281 A2 | 11/2015 | |
| WO | 2016090420 A1 | 6/2016 | |
| WO | 2016090436 A1 | 6/2016 | |
| WO | 2016191808 A1 | 12/2016 | |
| WO | 2017100866 A1 | 6/2017 | |
| WO | 2017106503 A1 | 6/2017 | |
| WO | 2017173493 A1 | 10/2017 | |
| WO | 2017184238 A1 | 10/2017 | |
| WO | 2017219096 A1 | 12/2017 | |
| WO | WO-2018080753 A1 * | 5/2018 | A61B 5/4836 |
| WO | WO2018080754 A1 * | 5/2018 | A61N 1/05 |
| WO | 2018106813 A1 | 6/2018 | |
| WO | 2019231794 A1 | 12/2019 | |

OTHER PUBLICATIONS

Crosby et al., "Modulation of activity and conduction in single dorsal column axons by kilohertz-frequency spinal cord stimulation," American Physiological Society, published online Oct. 19, 2016, 27 pp.

U.S. Appl. No. 17/065,282, by Medtronic, Inc. (Inventors: Dinsmoor et al), filed Oct. 7, 2020.

Vallejo et al., "Effects of Phase Polarity and Charge Balance Spinal Cord Stimulation on Behavior and Gene Expression in a Rat Model of Neuropathic Pain," Neuromodulation: Technology at the Neural Interface, vol. 23, No. 1, Apr. 2019, 10 pp.

"St. Jude's Prodigy Neurostimulator with Burst Technology," Medgadget, Mar. 20, 2014, 4 pp.

Abejon MD "Back pain coverage with spinal cord stimulation: A different treatment for each patient," International Neuromodulation Society. Jun. 10, 2015; 567, Abstract Only, 1 pp.

Abeloos MD "High density stimulation as an alternative to uncomfortable cervical tonic spinal cord stimulation: case report," International Neuromodulation Society 12th World Congress, Jun. 11-15, 2015, Abstract Only, 1 pp.

Breel et al., "High Density Stimulation: A novel programming paradigm for the treatment of chronic pain," International Neuromodulation Society (INS) 12th World Congress; Jun. 9, 2015, Abstract Only, 1 pp.

Cuellar MD PhD, et al., "Effect of high-frequency alternating current on spinal afferent nociceptive transmission," Neuromodulation: Technology at the Neural Interface; Jul.-Aug. 2013;16(4): pp. 318-327.

Cui et al., "Effect of spinal cord stimulation on tactile hypersensitivity in mononeuropathic rats is potentiated by simultaneous GABA. sub B. and adenosine receptor activation," Neuroscience Letters 247: Apr. 1998; pp. 183-186.

Cui et al., "Spinal cord stimulation attenuates augmented dorsal horn release of excitatory amino acids in mononeuropathy via a GABAergic mechanism," Pain 73, Oct. 1997, pp. 87-95.

De Ridder et al., "Burst spinal cord stimulation for limb and back pain," World neurosurgery, Nov. 2013; 80 (5):642-649, e641.

De Ridder MD PhD et al., "Burst spinal cord stimulation: toward paresthesia-free pain suppression," Neurosurgery. May 2010; 66(5): 986-990.

Downey, "Asynchronous Neuromuscular Electrical Stimulation," University of Florida, 2015, accessed on Jul. 18, 2016, 107 pp.

Duyvendak MD et al., "High density stimulation: a novel programming paradigm for the treatment of chronic back and leg pain," Abstracts, International Neuromodulation Society 12th World Congress: Jun. 11-15, 2015, 1 pp.

Gao et al., "Effects of spinal cord stimulation with "standard clinical" and higher frequencies on peripheral blood flow in rats," Brain Res., 1313: (2010) available online Dec. 3, 2009 pp. 53-61.

Grider DO/PhD et al., "High Frequency (1000 Hz) Stimulation Using Commercially Available Implantable Pulse Generator," North American Neuromodulation Society. Dec. 2013, Abstract Only, 2 pp.

Guan MD PhD et al., "Spinal cord stimulation-induced analgesia: electrical stimulation of dorsal column and dorsal roots attenuates dorsal horn neuronal excitability in neuropathic rats," Anesthesiology. Dec. 2010;113(6): pp. 1392-1405.

Guan, "Spinal Cord Stimulation: Neurophysiological and Neurochemical Mechanisms of Action" Curr Pain Headache Rep DOI 10.1007s11916-014-0260-4, Mar. 8, 2012, pp. 217-225.

Holsheimer, "Computer modelling of spinal cord stimulation and its contribution to therapeutic efficacy," Spinal Cord Aug. 1998, 36: pp. 531-540.

Hunt et al. The molecular dynamics of pain control. Nat Rev Neurosci. Feb. 2001;2(2):83-91.

Kemler MD et al., "Spinal cord stimulation in patients with chronic reflex sympathetic dystrophy," N Engl J Med, Aug. 31, 2000; 343(9):pp. 618-624.

Kilgore PhD et al., "Reversible Nerve Conduction Block Using Kilohertz Frequency Alternating Current," Neuromodulation. Aug. 2013, pp. 242-255.

Kumar et al., "Spinal cord stimulation versus conventional medical management for neuropathic pain: a multicentre randomised controlled trial in patients with failed back surgery syndrome," Pain Jul. 2007; 132(1-2): 179-188.

Likar et al., "High density spinal cord stimulation: a multi-center experience," Abstracts, International Neuromodulation Society 12th World Congress; Jun. 11-15, 2015, 1 pp.

Sweet MD et al., "High Frequency vs. Burst Stimulation Patterns for Dorsal Column Stimulation: The Importance of Charge," American Association of Neurological Surgeons, Abstract, Apr. 4, 2014, 2 pp.

Maeda et al., "Low frequencies, but not high frequencies of bi-polar spinal cord stimulation reduce cutaneous and muscle hyperalgesia induced by nerve injury," Pain; Feb. 2008; 138(1): pp. 143-152.

North MD et al., "Spinal cord stimulation versus repeated lumbosacral spine surgery for chronic pain: a randomized, controlled trial," Neurosurgery, Jan. 2005; 56(1): 98-106; discussion 106-107.

North MD et al., "Clinical outcomes of 1 kHz subperception spinal cord stimulation (SCS): Results of a prospective randomized controlled crossover trial," Abstracts, International Neuromodulation Society, Jun. 2015, 1 pp.

Ranck Jr. et al., "Which elements are excited in electrical stimulation of mammalian central nervous system: a review," Brain Research, Nov. 21, 1975; 98(3): pp. 417-440.

Replogle MD. et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective

(56) References Cited

OTHER PUBLICATIONS

U.S. filing date of the present application, and any foreign priority date that the particular month of publication is not in issue.
Sato et al., "Spinal cord stimulation reduces hypersensitivity through activation of opioid receptors in a frequency-dependent manner," Eur J Pain. Apr. 2013 (4): pp. 551-561, first published Oct. 5, 2012.
Song MD Phd. et al., "Efficacy of kilohertz-frequency and conventional spinal cord stimulation in rat models of different pain conditions, " Neuromodulation Jan. 2014; 17(3): pp. 226-234.
Schu MD, PhD. et al., "A prospective, randomised, double-blind, placebo-controlled study to examine the effectiveness of burst spinal cord stimulation patterns for the treatment of failed back surgery syndrome," Neuromodulation. Apr. 2014; 17(5): pp. 443-450.
Shechter MD et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
Maeda et al., "Increased c-fos immunoreactivity in the spinal cord and brain following spinal cord stimulation is frequency-dependent," Brain Res. Mar. 9, 2009; 1259: pp. 40-50, available online Jan. 6, 2009.
Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.
Smith et al., "Successful use of high-frequency spinal cord stimulation following traditional treatment failure," Stereotact Funct Neurosurg. Apr. 1, 2015; 93(3): pp. 190-193.
Wille MD et al., "Altering Conventional to High Density Spinal Cord Stimulation: An Energy Dose-Response Relationship in Neuropathic Pain Therapy," Neuromodulation 2016, Aug. 2016, 9 pp.
Maggi et al., "Effect of urethane anesthesia on the micturition reflex in capsaicin-treated rats." Journal of the Autonomic Nervous System, Jan. 1990, 30(3): 247-251.
Walter et al., "Inhibiting the hyperreflexic bladder with electrical stimulation in a spinal animal model." Neurourology and Urodynamics, 1993, 12:241-253. doi:10.1002/nau.1930120306. Applicant points out in accordance with MPEP 609.04(a) that the 1993 year of publication is sufficiently earlier than the effective U.S. filing date of the present application, and any foreign priority date that the particular month of publication is not in issue.
Hubscher et al., "Convergence and cross talk in urogenital neural circuitries," J. Neurophysiol 110: 1997-2005, first published Aug. 7, 2013, 9 pp.
Snellings et al., "Effects of stimulation site and stimulation parameters on bladder inhibition by electrical nerve stimulation," BJU International, Jul. 2012, pp. 136-143, first published Jan. 19, 2012.
Woock et al., "Activation and inhibition of the micturition reflex by penile afferents in the cat," Am J. Physiol Regul Intergre Comp Physiol, published Apr. 23, 2008, pp. R1880-R1889.
Youn et al., The Effect of High-Frequency Stimulation on Sensory Thresholds in Chronic Pain Patients, Stereotact Funct Neurosurg, Oct. 8, 2015, pp. 355-359.
International Search Report and Written Opinion of International Application No. PCT/US2020?055650, mailed Mar. 26, 2021, 10 pp.
Kent et al., "Instrumentation to record evoked potentials for closed-loop control of deep brain stimulation", 2011 Annual International Conference of the IEEE Engineering in Medicine and Biology Society, IEEE, Aug. 6, 2012, pp. 6777-6780.
First Examination Report from counterpart Australian Application No. 2020371537 dated Mar. 13, 2025, 3 pp.

\* cited by examiner

SUB-THRESHOLD STIMULATION BASED ON ECAP DETECTION

This application claims the benefit of U.S. Provisional Patent Application No. 62/926,188, filed on Oct. 25, 2019, the entire content of which is incorporated herein by reference.

TECHNICAL FIELD

This disclosure generally relates to electrical stimulation therapy, and more specifically, control of electrical stimulation therapy.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

An evoked compound action potential (ECAP) is synchronous firing of a population of neurons which occurs in response to the application of a stimulus including, in some cases, an electrical stimulus by a medical device. The ECAP may be detectable as being a separate event from the stimulus itself, and the ECAP may reveal characteristics of the effect of the stimulus on the nerve fibers. Electrical stimulation may be delivered to a patient by the medical device in a train of electrical pulses, and parameters of the electrical pulses may include a frequency, an amplitude, a pulse width, and a pulse shape. The parameters of the electrical pulses may be altered in response to sensory input, such as a parameter of ECAPs sensed in response to the train of electrical pulses. Such alterations may affect the patient's perception of the electrical pulses, or lack thereof.

SUMMARY

In general, systems, devices, and techniques are described for controlling electrical stimulation based on at least one stimulation threshold. For example, techniques of this disclosure may enable a medical device to determine, based on sensing one or more evoked compound action potential (ECAPs) signals, at least one stimulation threshold such as a perception threshold or a detection threshold related to the stimulation pulse or pulses that elicited the ECAP signals. A perception threshold may represent a characteristic ECAP value associated with a value for a stimulation parameter that defines pulses that are perceptible by the patient. A detection threshold may represent a characteristic ECAP value associated with a value for a stimulation parameter that defines pulses that elicit an ECAP signal measurable by a device. In some examples, the medical device may also adjust a stimulation parameter to define informed pulses based on stimulation levels of pulses (e.g., a control pulse) that elicit ECAP signals having a characteristic that achieves, or approximates, the stimulation threshold.

By identifying stimulation levels of pulses that elicit ECAP signals having a characteristic similar to the stimulation threshold, such as a perception threshold or detection threshold, a system can deliver electrical stimulation therapy to a patient at a level in which the patient is generally not able to perceive the electrical stimulation therapy or the system is not able to detect ECAP signals. This sub-threshold stimulation therapy may be configured to provide relief for patient symptoms such as chronic pain in the patient while reducing or eliminating uncomfortable sensations, uncomfortable jolts, or other side effects as compared to supra-threshold stimulation therapy. In some examples, sub-threshold stimulation therapy may still elicit therapeutic paresthesia or reduce the propagation of pain signals.

In one example, a medical device includes stimulation generation circuitry configured to deliver electrical stimulation therapy to a patient, wherein the electrical stimulation therapy comprises a plurality of therapy pulses; sensing circuitry configured to sense one or more evoked compound action potential (ECAP) signals, wherein the sensing circuitry is configured to sense each ECAP signal of the one or more ECAPs elicited by a respective control pulse of a plurality of control pulses; and processing circuitry configured to determine, based on the one or more ECAP signals, a stimulation level for the plurality of control pulses that achieves a stimulation threshold, determine, based on the stimulation level, a value of a stimulation parameter that at least partially defines the plurality of therapy pulses of the electrical stimulation therapy, and control the stimulation generation circuitry to deliver the electrical stimulation therapy to the patient according to the value of the stimulation parameter.

In another example, a method includes delivering, by stimulation generation circuitry, electrical stimulation therapy to a patient, wherein the electrical stimulation therapy comprises a plurality of therapy pulses, sensing, by sensing circuitry, one or more evoked compound action potential (ECAP) signals, wherein the sensing circuitry is configured to sense each ECAP signal of the one or more ECAPs elicited by a respective control pulse of a plurality of control pulses; determining, by processing circuitry and based on the one or more ECAP signals, a stimulation level for the plurality of control pulses that achieves a stimulation threshold; determining, by the processing circuitry and based on the stimulation level, a value of a stimulation parameter that at least partially defines the plurality of therapy pulses of the electrical stimulation therapy; and controlling, by the processing circuitry, the stimulation generation circuitry of to deliver the electrical stimulation therapy to the patient according to the value of the stimulation parameter.

In another example, a computer-readable medium includes instructions that, when executed by a processor, causes the processor to control stimulation generation circuitry to deliver electrical stimulation therapy to a patient, wherein the electrical stimulation therapy comprises a plurality of therapy pulses; control sensing circuitry to sense one or more evoked compound action potential (ECAP) signals, wherein the sensing circuitry is configured to sense each ECAP signal of the one or more ECAPs elicited by a respective control pulse of a plurality of control pulses; determine, based on the one or more ECAP signals, a stimulation level for the plurality of control pulses that achieves a stimulation threshold; determine, based on the stimulation level, a value of a stimulation parameter that at least partially defines the plurality of therapy pulses of the electrical stimulation therapy; and control the stimulation generation circuitry to deliver the electrical stimulation therapy to the patient according to the value of the stimulation parameter.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

Like reference characters denote like elements throughout the description and figures.

DETAILED DESCRIPTION

Figure 1:
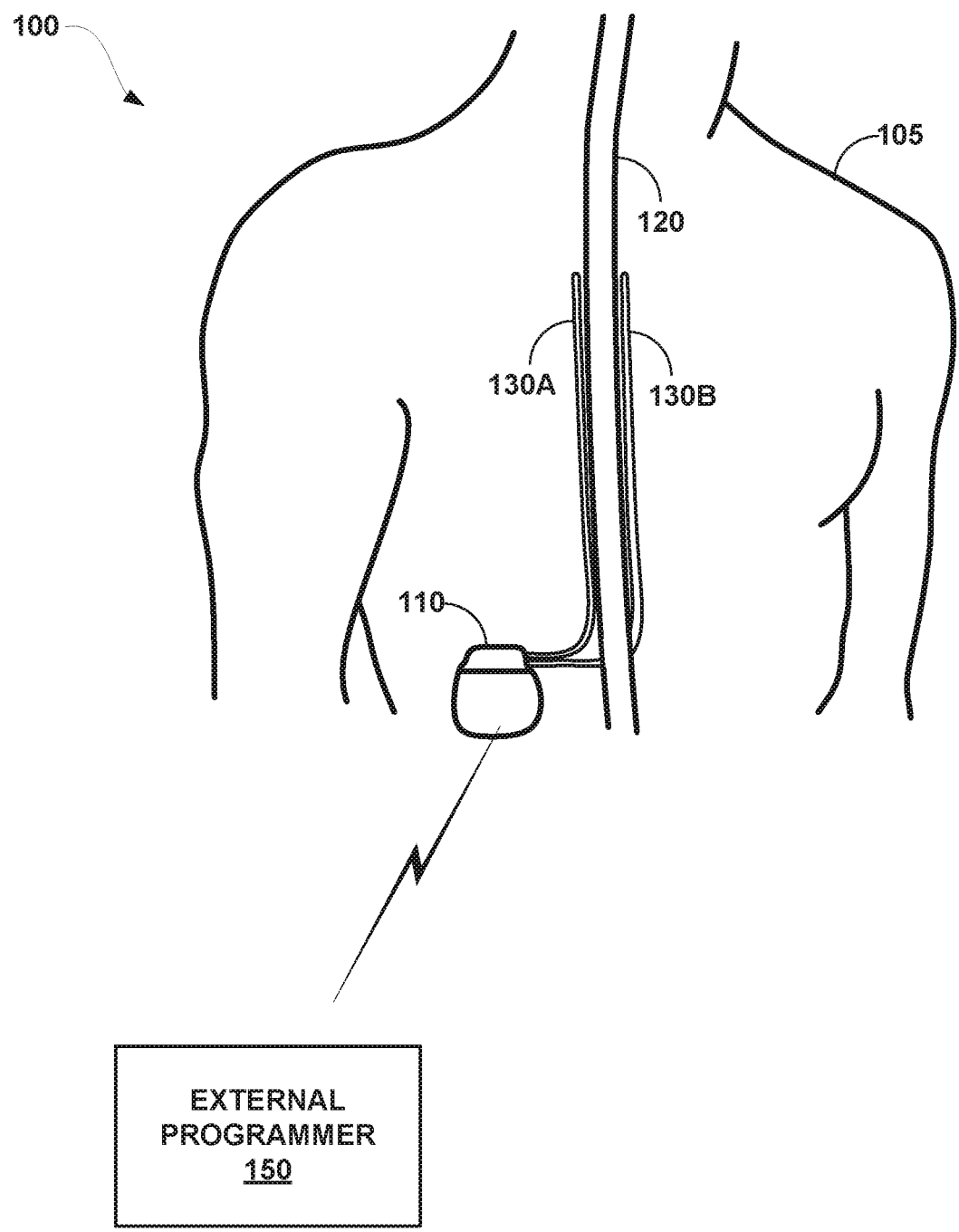
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes examples of medical devices, systems, and techniques for automatically adjusting electrical stimulation therapy delivered to a patient based on one or more characteristics of evoked compound action potentials (ECAPs) and a stimulation threshold. The ECAP signals may be sensed by a medical device in response to, in some examples, control stimulation pulses delivered by the medical device. Control stimulation pulses may or may not contribute to the therapy of (e.g., elicit a therapeutic effect for) a patient. Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, nervous system disorders, muscle disorders, etc. However, as the patient moves, the distance between the electrodes and the target tissue changes. Since neural recruitment is a function of stimulation intensity and distance between the target tissue and the electrodes, movement of the electrode closer to the target tissue may result in increased neural recruitment (e.g., possible painful sensations or adverse motor function), and movement of the electrode further from the target tissue may result in decreased efficacy of the therapy for the patient.

ECAPs can be used as a measure of neural recruitment because each ECAP signal represents the superposition of electrical potentials generated from a population of axons firing in response to an electrical stimulus (e.g., a stimulation pulse). Changes in a characteristic (e.g., an amplitude of a portion of the signal) of an ECAP signals occur as a function of how many axons have been activated by the delivered stimulation pulse. A system can monitor changes in the characteristic of the ECAP signal and use that change in the characteristic to adjust one or more stimulation parameter of the pulses (e.g., control pulses or informed pulses) delivered to the patient. For example, the system can reduce the intensity of stimulation pulses (e.g., reduce a current amplitude and/or pulse width) in response to detecting an increase in an amplitude of an ECAP signal.

In some examples, a clinician may desire to provide electrical stimulation therapy at an intensity that has some relation to a stimulation threshold. For example, a perception threshold may represent a characteristic ECAP value associated with a value for a stimulation parameter that defines pulses that are perceptible by the patient. Electrical stimulation therapy provided at some fraction below the perception threshold may provide some relief from the patient's symptoms without the therapy being perceived by the patient. As another example type of stimulation threshold, a detection threshold may represent a characteristic ECAP value that is associated with a value for a stimulation parameter that defines pulses that elicit a detectable ECAP signal. Since a detectable ECAP signal indicates that nerve fibers have been recruited, thus indicating that the patient may perceive the stimulation, a clinician may desire to deliver stimulation therapy at some fraction below the detection threshold.

The stimulation level of pulses to achieve, or result in some fraction of, the perception threshold and the detection threshold required for the patient to perceive the stimulation and for the medical device to detect ECAPs occurring in response to the stimulation, respectively, may change over a period of time based on a number of factors. A distance between electrodes of the medical device and target nervous tissue of the patient may affect the intensity of pulses required to achieve the perception threshold and the detection threshold. For example, if the distance between the electrodes and the nervous tissue decreases, the stimulation level of a pulse required to achieve the perception threshold and the detection threshold may likewise decrease. Alternatively, if the distance between the electrodes and the nervous tissue increases, the stimulation level of a pulse required to achieve the perception threshold and the detection threshold may likewise increase. In some examples, the distance between the electrodes and the nervous tissue changes according to patient posture, patient activity, patient movements, or lead migration over time. Thus, it may be beneficial for the medical device to occasionally, repeatedly, or continuously, determine the stimulation level required to elicit a characteristic of an ECAP signal that achieves, or is similar to, a perception threshold and the detection threshold in order to maintain consistent delivery of electrical stimulation. However, it may be difficult use an ECAP signal as feedback to control stimulation therapy when the desired stimulation therapy may not elicit many, if any, patient perception and/or ECAP signals.

As described herein, a system may be configured to employ one or more techniques to deliver stimulation therapy based on one or more stimulation thresholds. For example, a perception threshold value may be less than a detection threshold value for a patient. In this way, electrical stimulation delivered to a patient by a medical device may be perceived by the patient at an intensity which does not elicit detectable ECAPs by the system. In such examples, it may be difficult to determine the perception threshold based on sensed ECAPs since electrical stimulation delivered at or near the perception threshold value does not elicit ECAPs that are detectible by the medical device. One or more techniques of this disclosure enable the medical device to periodically determine the stimulation level of pulses required to achieve the detection threshold and deliver sub-perception threshold stimulation to the patient at a fraction of the detection threshold. By periodically determining the stimulation level associated with the detection threshold, the medical device may be configured to maintain a consistent level of sub-perception therapy as the distance between the electrodes of the medical device and the target tissue changes over time and/or with patient movement. Additionally, in examples where the perception threshold is greater than the detection threshold, one or more techniques of this disclosure may enable the medical device to periodically determine the perception threshold and changes to the stimulation level required to achieve the perception threshold. By periodically determining the stimulation level associated with the perception threshold, the medical device may be configured to maintain a consistent level of sub-perception therapy as the distance between the electrodes of the medical device and the target tissue changes.

Although the techniques described herein may monitor ECAPs elicited by one or more pulses (e.g., a control pulse that may be therapeutic or non-therapeutic) may be used to elicit ECAP signals in other examples. Synchronous nerve impulses detectable as the ECAP signal travel quickly along the nerve fiber after the delivered stimulation pulse first depolarizes the nerve. If the stimulation pulse delivered by first electrodes has a pulse width that is too long, different electrodes configured to sense the ECAP will sense the stimulation pulse itself as an artifact that obscures the lower amplitude ECAP signal. However, the ECAP signal loses fidelity as the electrical potentials propagate from the electrical stimulus because different nerve fibers propagate electrical potentials at different speeds. Therefore, sensing the ECAP at a far distance from the stimulating electrodes may avoid the artifact caused by a stimulation pulse with a long pulse width, but the ECAP signal may lose fidelity needed to detect changes to the ECAP signal that occur when the electrode to target tissue distance changes. In other words, the system may not be able to identify, at any distance from the stimulation electrodes, ECAPs from stimulation pulses configured to provide a therapy to the patient.

In some examples, a medical device may be configured to deliver control pulses or a combination of a plurality of control pulses and a plurality of informed pulses. The plurality of control pulses, in some cases, may be therapeutic and contribute to therapy received by the patient. In other examples, the plurality of the control pulses may be non-therapeutic and not contribute to the therapy received by the patient. Put another way, the control pulses configured to elicit detectable ECAPs may or may not contribute to alleviating the patient's condition or symptoms of the patient's condition. In contrast to control pulses, informed pulses may not elicit a detectable ECAP or the system may not utilize ECAPs from informed pulses as feedback to control therapy. Therefore, the medical device or other component associated with the medical device may determine values of one or more stimulation parameters that at least partially define the informed pulses based on an ECAP signal elicited by a control pulse instead. In this manner, the informed pulse may be informed by the ECAP elicited from a control pulse. The medical device or other component associated with the medical device may determine values of one or more stimulation parameters that at least partially define the control pulses based on an ECAP signal elicited by previous control pulse.

In one example described herein, a medical device is configured to deliver a plurality of informed pulses configured to provide a therapy to the patient and a plurality of control pulses. At least some of the control pulses may elicit a detectable ECAP signal without the primary purpose of providing a therapy to the patient. The control pulses may be interleaved with the delivery of the informed pulses. For example, the medical device may alternate the delivery of informed pulses with control pulses such that a control pulse is delivered, and an ECAP signal is sensed, between consecutive informed pulses. In some examples, multiple control pulses are delivered, and respective ECAP signals sensed, between the delivery of consecutive informed pulses. In some examples, multiple informed pulses will be delivered between consecutive control pulses. In any case, the informed pulses may be delivered according to a predetermined pulse frequency selected so that the informed pulses can produce a therapeutic result for the patient. One or more control pulses are then delivered, and the respective ECAP signals sensed, within one or more time windows between consecutive informed pulses delivered according to the predetermined pulse frequency. In this manner, a medical device can administer informed pulses from the medical device uninterrupted while ECAPs are sensed from control pulses delivered during times at which the informed pulses are not being delivered. In other examples described herein, ECAPs are sensed by the medical device in response to the informed pulses delivered by the medical device, and control pulses are not used to elicit ECAPs.

Based on one or more characteristics of detected ECAPs, the system may adjust one or more parameters that at least partially define the informed pulses and/or control pulses, if delivered. For example, in some cases it may be desirable to maintain sub-perception stimulation therapy delivered to the patient. In other words, it may be beneficial to alleviate chronic pain in the patient while avoiding or reducing the inducement of side-effects that may not be perceived as reducing symptoms. One or more characteristics of ECAPs may provide an indication of whether a patient is able to perceive electrical stimulation. A perception threshold may define a characteristic of an ECAP signal that is elicited when a pulse is delivered at a certain stimulation level. This stimulation level may be used by the system to at least partially define the informed pulses in which the patient is able to perceive the informed pulses. For example, the patient may not be able to perceive informed pulses delivered at a first pulse amplitude that is below the perception threshold. However, the patient may be able to perceive informed pulses delivered at a second pulse amplitude, where the second pulse amplitude is greater than the first pulse amplitude and the second pulse amplitude results in a characteristic of the ECAP signal that is greater than the perception threshold. Other parameters besides pulse amplitude may contribute to the stimulation level associated with the perception threshold. Pulse width or pulse frequency may contribute to stimulation level (e.g., a stimulation intensity) as perceived by the patient and be altered to deliver stimulation above and below a perception threshold.

As discussed above, the distance between the electrodes of the medical device and the target tissues changes according to patient posture, patient activity, patient movements, or lead migration over time. Additionally, the distance between the electrodes and the target tissue may briefly change due to any one of a cough, a sneeze, a Valsalva maneuver, or another transient patient movement. The stimulation level required to achieve the perception threshold may change, and in some cases may greatly change when the position of the electrodes moves relative to the target tissue. For instance, if the electrodes move farther from the target tissue, the stimulation level may increase and when the electrodes move closer to the target tissue, the stimulation level may decrease. Thus, it may be beneficial for the medical device to periodically determine the stimulation level associated with the perception threshold and adjust the one or more parameters of the informed pulses such that the patient receives sub-perception therapy.

In some cases, it may be difficult for the medical device to determine the stimulation level that results in the perception threshold, since the stimulation pulses (e.g., informed pulses or control pulses) may be delivered at an amplitude in which the medical device is unable to detect ECAPs, either because the ECAP signal is too small or the stimulation does not elicit an ECAP signal. In this manner, a detection threshold of the stimulation pulses may be greater than the perception threshold of the stimulation pulses. The detection threshold may be associated with one or more parameter values of the informed pulses in which ECAPs elicited from to the informed pulses, or control pulses interleaved with informed pulses, are detectable by the medical device. Like the stimulation level associated with the perception threshold, the stimulation level associated with the detection threshold may change depending on the distance between the electrodes of the medical device and the target tissue. As such, to maintain sub-perception therapy stimulation of the patient in cases where the detection threshold is greater than the perception threshold, the medical device may periodically determine the stimulation level required to achieve the detection threshold, and deliver the informed pulses at a fraction of the stimulation level in an attempt to deliver informed pulses below the perception threshold.

In some examples, to ascertain the stimulation level of the detection threshold, the medical device is configured to determine one or more baseline parameter values of the stimulation pulses where if the stimulation pulses are delivered at the one or more baseline parameter values, the medical device is configured to detect at least a threshold ratio of ECAPs (which may be elicited and detected from informed pulses or control pulses interleaved with the informed pulses) that may represent a desired detection threshold for that patient. The ratio of ECAPs that are detected is the ratio of detected ECAPs to the total number of stimulation pulses for which ECAPs were attempted to be detected. The ratio of ECAPs that are detectable by the medical device may increase as the one or more parameters that at least partially define the intensity of the stimulation pulses are increased. If the ratio of ECAPs that are detectable by the medical device is lower than the threshold ratio, the medical device may increase the value of one or more stimulation parameters in an attempt to increase the ratio of detected ECAP signals. Alternatively, if the ratio of ECAPs that are detectable by the medical device is greater than the threshold ratio, the medical device may decrease the value of the one or more stimulation parameters in an attempt to decrease the ratio of detected ECAP signals. In this manner, the medical device may attempt to maintain stimulation parameter values at the stimulation level that achieves the detection threshold represented by the threshold ratio of detected ECAPs or at some fraction less than the detection threshold represented by the threshold ratio. Once the stimulation level is determined by the medical device, the medical device may deliver stimulation pulses (such as informed pulses and/or control pulses) at a fraction of the stimulation level for the detection threshold, such that the patient is not able to perceive the informed pulses.

Informed pulses and control pulses are generally described herein as different stimulation pulses reflective of different types of electrical stimulation. However, the different types of electrical stimulation, and their respective pulses, may be described with different attributes. For example, a first type of electrical stimulation may include first pulses (such as informed pulses) configured to primarily contribute to a therapy for a patient. The first pulses of this first type of electrical stimulation may also have one or more characteristics (e.g., a pulse width) that prevent or reduce the ability of the system to detect ECAP signals elicited from the first pulses of the first type of electrical stimulation because an artifact representative of the first pulses themselves overlaps with and obscures at least a portion of the respective elicited ECAP signal. A second type of electrical stimulation may include second pulses (such as control pulses) defined by one or more parameter values selected to elicit ECAP signals that are sensed and detectable by the system. The second pulses may thus be referred to as "sense pulses" or "test pulses" since the second pulses are configured to elicit a detectable ECAP signal. For example, the second pulses of the second type of electrical stimulation may improve the detectability of the ECAP signal such as to not generate an artifact that obscures the ECAP signals or otherwise prevents or reduces the ability of the system to detect the ECAP signal from each of the second pulses. In addition, the second pulses may be defined by parameter values selected to elicit an ECAP signal that is used to at least modify one or more parameter values of the first pulses of the first type of electrical stimulation. The first pulses may thus differ from the second pulses by at least one parameter (e.g., current and/or voltage amplitude, pulse width, and/or frequency). The first pulses may be at least partially interleaved with at least some of the second pulses. For example, the system may alternate delivery of one first pulse with delivery of one second pulse. In another example, the number of first pulses may differ from the number of second pulses by a ratio or percentage. The ratio could be 1:1 when the first and second pulses are fully interleaved. The ratio could be 10:1 first pulses to second pulses in examples in which the second pulses are delivered less frequently than the first pulses. In other examples, the ratio could be 1:4 first pulses to second pulses when the second pulses, and respective sensed ECAP signals) occur more frequently than the first pulses. The second pulses may or may not contribute to a therapy and/or sensation perceived by the patient, but the primary purpose of the second pulses is to elicit respective ECAP signals that are detectable by the system separate from any sensed artifacts representative of the second pulses themselves.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating an example system 100 that includes an implantable medical device (IMD) 110 configured to deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. In addition to electrical stimulation therapy, IMD 110 may also be configured to generate and deliver control pulses configured to elicit ECAP signals instead of contributing to the therapy of informed pulses. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of informed pulses are typically predetermined parameter values determined prior to delivery of the informed pulses. However, in some examples, system 100 changes one or more parameter values automatically based on one or more factors or based on user input.

In addition to stimulation informed pulses, an ECAP test stimulation program may define stimulation parameter values that define control pulses delivered by IMD 110 through at least some of the electrodes of leads 130. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program defines when the control pulses are to be delivered to the patient based on the frequency and/or pulse width of the informed pulses. However, the stimulation defined by each ECAP test stimulation program are not intended to provide or contribute to therapy for the patient.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, and pulse rate (e.g., pulse frequency) for stimulation pulses delivered by IMD 110 according to that program.

Furthermore, IMD 110 may be configured to deliver control stimulation to patient 105 via a combination of electrodes of leads 130, alone or in combination with an electrode carried by or defined by an outer housing of IMD 110. The tissue targeted by the control stimulation may be the same or similar tissue targeted by the electrical stimulation therapy, but IMD 110 may deliver control stimulation pulses via the same, at least some of the same, or different electrodes. Since control stimulation pulses can be delivered in an interleaved manner with informed pulses, a clinician and/or user may select any desired electrode combination for informed pulses. Like the electrical stimulation therapy, the control stimulation may be in the form of electrical stimulation pulses or continuous waveforms. In one example, each control stimulation pulse may include a balanced, bi-phasic square pulse that employs an active recharge phase. However, in other examples, the control stimulation pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 130. In cases where the control stimulation pulses are applied to spinal cord 120, the signal may be sensed by IMD 110 from spinal cord 120.

IMD 110 can deliver control stimulation to a target stimulation site within patient 105 via the electrodes of leads 130 according to one or more ECAP test stimulation programs. The one or more ECAP test stimulation programs may be stored in a storage device of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 105. In some examples, IMD 110 delivers control stimulation to patient 105 according to multiple ECAP test stimulation programs.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control electrical stimulation therapy (e.g., informed pulses) and control stimulation (e.g., control pulses). For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

In this disclosure, efficacy of electrical stimulation therapy may be indicated by one or more characteristics (e.g. an amplitude of or between one or more peaks or an area under the curve of one or more peaks) of an action potential that is evoked by a stimulation pulse delivered by IMD 110 (i.e., a characteristic of the ECAP signal). Electrical stimulation therapy delivery by leads 130 of IMD 110 may cause neurons within the target tissue to evoke a compound action potential that travels up and down the target tissue, eventually arriving at sensing electrodes of IMD 110. Furthermore, control stimulation may also elicit at least one ECAP, and ECAPs responsive to control stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

In one example, each informed pulse may have a pulse width greater than approximately 300 μs, such as between approximately 300 μs and 1200 μs (i.e., 1.2 milliseconds) in some examples. At these pulse widths, IMD 110 may not sufficiently detect an ECAP signal because the informed pulse is also detected as an artifact that obscures the ECAP signal. If ECAPs are not adequately recorded, then ECAPs arriving at IMD 110 cannot be compared to the target ECAP characteristic (e.g. a target ECAP amplitude), and electrical therapy stimulation cannot be altered according to responsive ECAPs. When informed pulses have these longer pulse widths, IMD 110 may deliver control stimulation in the form of control pulses. The control pulses may have pulse widths of less than approximately 300 μs, such as a bi-phasic pulse with each phase having a duration of approximately 100 μs. Since the control pulses may have shorter pulse widths than the informed pulses, the ECAP signal may be sensed and identified following each control pulse and used to inform IMD 110 about any changes that should be made to the informed pulses (and control pulses in some examples). In general, the term "pulse width" refers to the collective duration of every phase, and interphase interval when appropriate, of a single pulse. A single pulse includes a single phase in some examples (i.e., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 μs, a negative phase lasting 100 μs, and an interphase interval lasting 30 μs defines a pulse width of 230 μs).

As described, the example techniques for adjusting stimulation parameter values for informed pulses are based on comparing the value of a characteristic of a measured ECAP signal to a target ECAP characteristic value, which may or may not be based on a stimulation threshold (e.g., a perception threshold or detection threshold). During delivery of control stimulation pulses defined by one or more ECAP test stimulation programs, IMD 110, via two or more electrodes interposed on leads 130, senses electrical potentials of tissue of the spinal cord 120 of patient 105 to measure the electrical activity of the tissue. IMD 110 senses ECAPs from the target tissue of patient 105, e.g., with electrodes on one or more leads 130 and associated sense circuitry. In some examples, IMD 110 receives a signal indicative of the ECAP from one or more sensors, e.g., one or more electrodes and circuitry, internal or external to patient 105. Such an example signal may include a signal indicating an ECAP of the tissue of patient 105. Examples of the one or more sensors include one or more sensors configured to measure a compound action potential of patient 105, or a physiological effect indicative of a compound action potential. For example, to measure a physiological effect of a compound action potential, the one or more sensors may be an accelerometer, a pressure sensor, a bending sensor, a sensor configured to detect a posture of patient 105, or a sensor configured to detect a respiratory function of patient 105. However, in other examples, external programmer 150 receives a signal indicating a compound action potential in the target tissue of patient 105 and transmits a notification to IMD 110.

In the example of FIG. 1, IMD 110 described as performing a plurality of processing and computing functions. However, external programmer 150 instead may perform one, several, or all of these functions. In this alternative example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more stimulation parameter that defines the electrical stimulation informed pulses and, in some examples, control pulses, delivered to patient 105.

In the example techniques described in this disclosure, the control stimulation parameters and the target ECAP characteristic values may be initially set at the clinic but may be set and/or adjusted at home by patient 105. For example, the target ECAP characteristics may be changed to match or be a fraction of a stimulation threshold. Once the target ECAP characteristic values are set, the example techniques allow for automatic adjustment of informed pulse parameters to maintain consistent volume of neural activation and consistent perception of therapy for the patient when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. IMD 110 may perform these changes without intervention by a physician or patient 105.

In some examples, the system changes the target ECAP characteristic value over a period of time, such as according to a change to a stimulation threshold (e.g., a perception threshold or detection threshold). The system may be programmed to change the target ECAP characteristic in order to adjust the intensity of informed pulses to provide varying sensations to the patient (e.g., increase or decrease the volume of neural activation). In one example, a system may be programmed to oscillate a target ECAP characteristic value between a maximum target ECAP characteristic value and a minimum target ECAP characteristic value at a predetermined frequency to provide a sensation to the patient that may be perceived as a wave or other sensation that may provide therapeutic relief for the patient. The maximum target ECAP characteristic value, the minimum target ECAP characteristic value, and the predetermined frequency may be stored in the storage device of IMD 110 and may be updated in response to a signal from external programmer 150 (e.g., a user request to change the values stored in the storage device of IMD 110). In other examples, the target ECAP characteristic value may be programed to steadily increase or steadily decrease to a baseline target ECAP characteristic value over a period of time. In other examples, external programmer 150 may program the target ECAP characteristic value to automatically change over time according to other predetermined functions or patterns. In other words, the target ECAP characteristic value may be programmed to change incrementally by a predetermined amount or predetermined percentage, the predetermined amount or percentage being selected according to a predetermined function (e.g., sinusoid function, ramp function, exponential function, logarithmic function, or the like). Increments in which the target ECAP characteristic value is changed may be changed for every certain number of pulses or a certain unit of time. Although the system may change the target ECAP characteristic value, received ECAP signals may still be used by the system to adjust one or more parameter values of the informed pulses and/or control pulses in order to meet the target ECAP characteristic value.

It may be desirable to maintain a sub-perception level of therapy in patient 105. To maintain sub-perception therapy, IMD 110 may periodically determine the stimulation level that achieves the perception threshold of patient 105. The perception threshold may be a characteristic ECAP value from an ECAP signal, which may be associated with the stimulation level such as values one or more parameters of the plurality of informed pulses delivered to patient 105 by IMD 110. The one or more parameters, for example, may include stimulation electrode combination, electrode polarity, current or voltage amplitude, pulse width, pulse rate, pulse shape, an area under the pulse, or any combination thereof. ECAPs provide a reliable metric for determining the stimulation level of the perception threshold of patient 105. In other words, one or more characteristics of an ECAP signal sensed by IMD 110 may indicate whether patient 105 can perceive therapy delivered by IMD 110 or an extent to which the therapy is perceived by patient 105. Patient perception of electrical stimulation therapy delivered to patient 105 may change as a distance between leads 130 and the target tissue of spinal cord 120 changes. For example, if one or more parameters of the informed pulses delivered to patient 105 by IMD 110 remain constant and the distance between leads 130 and the target tissue of spinal cord 120 decreases, patient 105 may experience a stronger perception of the informed pulses. Additionally, if one or more parameters of the informed pulses delivered to patient 105 by IMD 110 remain constant and the distance between leads 130 and the target tissue of spinal cord 120 increases, patient 105 may experience a weaker perception of the informed pulses.

In some examples, IMD 110 includes stimulation generation circuitry configured to deliver the electrical stimulation therapy to patient 105. The electrical stimulation therapy includes a plurality of informed pulses. The stimulation generation circuitry is additionally configured to deliver a plurality of control pulses, where the plurality of control pulses is interleaved with at least some informed pulses of the plurality of informed pulses. In some examples, IMD 110 includes sensing circuitry configured to detect a plurality of ECAPs, where the sensing circuitry is configured to detect each ECAP of the plurality of ECAPs after a control pulse of the plurality of control pulses and prior to a subsequent informed pulse of the plurality of informed pulses. In this manner, IMD detects ECAPs in response to the delivery of control pulses, and a characteristic of the ECAP signals may indicate an efficacy (e.g., a volume of tissue activation) of the plurality of informed pulses.

Additionally, in some examples, IMD 110 includes processing circuitry configured to determine, based on the plurality of ECAPs detected by the sensing circuitry of IMD 110 in response to the plurality of control pulses, at least one of a stimulation level for a perception threshold or a detection threshold. If a value of the first stimulation parameter of the electrical stimulation therapy is delivered above the stimulation level associated with the perception threshold, patient 105 is capable of perceiving the electrical stimulation therapy. Additionally, the sensing circuitry of IMD 110 is configured to detect at least some ECAPs of the plurality of ECAPs which occur while a magnitude of the second parameter of the electrical stimulation therapy is greater than the detection threshold or otherwise associated with a characteristic ECAP value greater than the detection threshold. In this manner, if electrical stimulation therapy is delivered above the stimulation level of the detection threshold, IMD 110 is capable of detecting responsive ECAPs. In some examples, the first parameter and the second parameter include a current amplitude. In other examples, the first parameter and the second parameter include a voltage amplitude.

IMD 110 may control the stimulation generation circuitry to deliver the electrical stimulation therapy to patient 105 based on at least one of the perception threshold or the detection threshold. In some examples, to control the stimulation generation circuitry to deliver the electrical stimulation therapy to the patient based on the perception threshold, IMD 110 is configured to direct the stimulation generation circuitry to deliver the plurality of informed pulses at a fraction of the stimulation level associated with the perception threshold. Additionally, to control the stimulation generation circuitry to deliver the electrical stimulation therapy to the patient based on the detection threshold, IMD 110 is configured to direct the stimulation generation circuitry to deliver the plurality of informed pulses at a fraction of, and less than, the stimulation level associated with the detection threshold. In some examples, the fraction of the stimulation level is greater than 0.50 and less than 0.99 and the fraction of the stimulation level of the detection threshold is greater than 0.50 and less than 0.99. In examples in which the ECAP signals are detected off of control pulses, the detection threshold and/or perception threshold may be set to the characteristic of the ECAP signal from the control pulses. However, the stimulation parameter value that defines the informed pulses may be determined by applying a gain value to scale the parameter value of the control pulses to the stimulation parameter of the informed pulses.

In some examples, IMD 110 is configured to periodically determine the stimulation level of the perception threshold at which patient 105 can perceive informed pulses delivered by IMD 110. A frequency in which IMD 110 determines the stimulation level of the perception threshold may be a predetermined frequency (e.g., programmed into a storage device of IMD 110). In some cases, external programmer 150 may be configured to set or update the predetermined frequency. In other cases, processing circuitry of IMD 110 may be configured to set or update the predetermined frequency based on data collected by one or more sensors (e.g., electrodes, accelerometers, temperature sensors, pressure sensors, optical sensors, or any combination thereof) of IMD 110. IMD 110 may, in some cases, measure the stimulation level for the perception threshold of patient 105 at the predetermined frequency. For example, if the predetermined frequency is one measurement per hour, IMD 110 may determine the stimulation level for the perception threshold of patient 105 once per hour.

IMD 110 may be configured to deliver a first set of stimulation pulses (e.g., informed pulses or control pulses) at a first pulse amplitude. The first set of stimulation pulses is, in some examples, delivered by IMD 110 based on a previous stimulation level of the perception threshold measurement. For example, to deliver sub-perception threshold, IMD 110 may deliver electric stimulation therapy at a fraction of the stimulation level that resulted in the characteristic ECAP value at the perception threshold determined by a perception threshold measurement. However, over a period of time after the previous perception threshold measurement, the actual stimulation level that results in the perception threshold may change. To obtain an updated perception threshold, IMD 110 performs another perception threshold measurement. When IMD 110 determines that a perception threshold measurement must be made, IMD 110 is configured to deliver a second set of stimulation pulses that being a fraction of, and less than, the first pulse amplitude, and iteratively increases (e.g., by a predetermined amount) the pulse amplitude for a predetermined increase, a predetermined number of pulses, or until the new stimulation level for the perception threshold is detected. To determine the stimulation level of the perception threshold, the processing circuitry is configured to detect ECAP signals sensed by the sensing circuitry and determine a characteristic ECAP value from the ECAP signal. For the case where the stimulation pulses are control pulses, the ECAP signals are sensed after the stimulation generation circuitry delivers each respective control pulse and before a subsequent delivery of any other stimulation pulse. Responsive to IMD 110 determining that the patient can begin to perceive the stimulation pulse, IMD 110 may determine that the characteristic value of an ECAP signal associated with patient perception is the new perception threshold. In addition, IMD 110 may determine that the stimulation parameter value that at least partially defined the stimulation pulse that elicited the ECAP signal associated with the new perception threshold is the stimulation parameter value (e.g., stimulation level) that will be used as being associated with the new perception threshold. IMD 110 may determine to deliver subsequent stimulation pulses based on that stimulation parameter value. In some examples, the at least one characteristic value of the ECAP signal includes one or more a peak current amplitude, a peak voltage amplitude, a gradient, and an area under the ECAP.

In addition to determining the stimulation level of the perception threshold, IMD 110 may be configured to determine the stimulation level of the detection threshold. In some examples, processing circuitry may determine the stimulation level for the detection threshold to be when the characteristic value of the ECAP signal is first detectable as the stimulation pulse intensity of stimulation pulses is being increased. In another example, the processing circuitry may determine the stimulation level for the detection threshold based a set of consecutive stimulation pulses (e.g., a set of informed pulses or a set of control pulses). A threshold ratio of detected ECAP signals (e.g., a detectable characteristic value of an ECAP signal) may refer to the number respective ECAP signals detected from a set of consecutively delivered stimulation pulses to the total number of pulses in the set of consecutively determined stimulation pulses. 100 percent threshold ratio would indicate that an ECAP signal is detected after each pulse in the set of consecutive stimulation pulses. When using the threshold ratio to determine whether or stimulation is being delivered appropriately with respect to the detection threshold, IMD 110 may determine the ratio of ECAP signals detected from the total number of consecutive stimulation pulses delivered. If the ratio of ECAP signals is greater than the threshold ratio, IMD 110 may determine that the stimulation level for the detection threshold has decreased and/or reduce the stimulation parameter value for subsequent stimulation pulses (e.g., informed pulses and/or control pulses). If the ratio of ECAP signals is less than the threshold ratio, IMD 110 may determine that the stimulation level for the detection threshold has increased and/or increase the stimulation parameter value for subsequent stimulation pulses (e.g., informed pulses and/or control pulses). In this manner, IMD 110 may adjust stimulation parameter values even when an ECAP signal is not detectable after each stimulation pulse that was delivered.

As described herein, IMD 110 may be configured to determine the stimulation level for the perception threshold and the detection threshold based on ECAPs sensed in response to informed pulses and/or control pulses (e.g., the ECAPs are evoked by control pulses). Indeed, in cases in which ECAP signals are detectable from informed pulses, IMD 110 may be configured to determine the stimulation level for the perception threshold and the detection threshold based on ECAPs elicited by informed pulses.

Although in one example IMD 110 takes the form of an SCS device, in other examples, IMD 110 takes the form of any combination of deep brain stimulation (DBS) devices, implantable cardioverter defibrillators (ICDs), pacemakers, cardiac resynchronization therapy devices (CRT-Ds), left ventricular assist devices (LVADs), implantable sensors, orthopedic devices, or drug pumps, as examples. Moreover, techniques of this disclosure may be used to determine stimulation thresholds (e.g., perception thresholds and detection thresholds) associated any one of the aforementioned IMDs and then use a stimulation threshold to inform the intensity (e.g., stimulation levels) of therapy.

Figure 2:
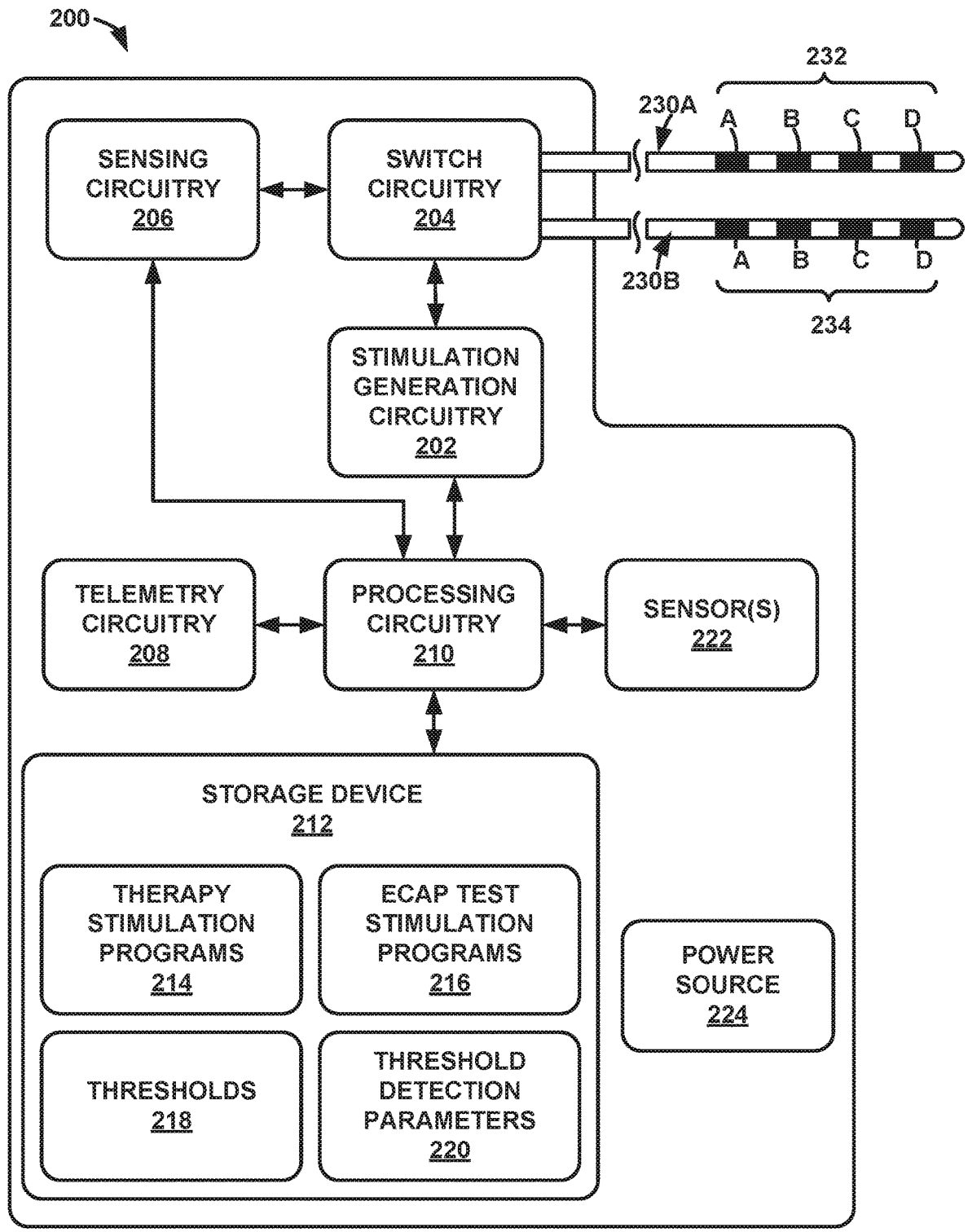
FIG. 2 is a block diagram illustrating an example configuration of components of an implantable medical device (IMD), in accordance with one or more techniques of this disclosure.

FIG. 2 is a block diagram illustrating an example configuration of components of IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, telemetry circuitry 208, processing circuitry 210, storage device 212, sensor(s) 222, and power source 224.

In the example shown in FIG. 2, storage device 212 stores therapy stimulation programs 214 and ECAP test stimulation programs 216 in separate memories within storage device 212 or separate areas within storage device 212. Storage device 212 also stores thresholds 218 and threshold detection parameters 220. Each stored therapy stimulation program of therapy stimulation programs 214 defines values for a set of electrical stimulation parameters (e.g., a stimulation parameter set), such as a stimulation electrode combination, electrode polarity, current or voltage amplitude, pulse width, pulse rate, and pulse shape. Each stored ECAP test stimulation programs 216 defines values for a set of electrical stimulation parameters (e.g., a control stimulation parameter set), such as a stimulation electrode combination, electrode polarity, current or voltage amplitude, pulse width, pulse rate, and pulse shape. ECAP test stimulation programs 216 may also have additional information such as instructions regarding when to deliver control pulses based on the pulse width and/or frequency of the informed pulses defined in therapy stimulation programs 214.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 monitors signals from any combination of electrodes 232, 234. In some examples, sensing circuitry 206 includes one or more amplifiers, filters, and analog-to-digital converters. Sensing circuitry 206 may be used to sense physiological signals, such as ECAPs. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via telemetry circuitry 208. Updates to the therapy stimulation programs 214 and ECAP test stimulation programs 216 may be stored within storage device 212. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to therapy stimulation programs 214 and ECAP test stimulation programs 216 stored in storage device 212 to apply stimulation parameter values specified by one or more of programs, such as amplitude, pulse width, pulse rate, and pulse shape of each of the stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2, in other examples, sensing circuitry 206 may be in a separate housing from IMD 200 and may communicate with processing circuitry 210 via wired or wireless communication techniques. In some examples, one or more of electrodes 232 and 234 are suitable for sensing the ECAPs. For instance, electrodes 232 and 234 may sense the voltage amplitude of a portion of the ECAP signals, where the sensed voltage amplitude is a characteristic the ECAP signal.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store therapy stimulation programs 214, ECAP test stimulation programs 216, thresholds 218, and threshold detection parameters 220.

In some examples, IMD 200 is configured to determine a stimulation threshold, such as at least one of a perception threshold or a detection threshold. The perception threshold may be represented by a characteristic ECAP value and/or a first set of values of one or more parameters of informed pulses delivered to patient 105 by stimulation generation circuitry 202. If stimulation generation circuitry 202 delivers the informed pulses at or above the first set of values which represent the perception threshold, patient 105 may perceive, or feel, the informed pulses (e.g., the characteristic ECAP value would indicate that the patient perceived that stimulation. Additionally, the detection threshold may be represented by a characteristic ECAP value and/or a second set of values of one or more parameters of informed pulses delivered to patient 105. If stimulation generation circuitry 202 delivers the informed pulses at or above the second set of values which represent the detection threshold, sensing circuitry 206 may be configured to detect all, or at least a fraction of, ECAP signals elicited by respective stimulation pulses (e.g., informed pulses and/or control pulses) delivered to patient 105. The perception threshold and the detection threshold may be stored in storage device 212 as part of thresholds 218. In some examples, a threshold ratio of ECAP signals may be associated with a detection threshold and also stored by thresholds 218.

Based on the perception threshold, the detection threshold, or other single stimulation threshold or combination thereof, processing circuitry 210 may set or update therapy stimulation programs 214 and ECAP test stimulation programs 216 (e.g., associated stimulation levels or parameter values indicative of those stimulation levels). In this manner, IMD 200 is configured to customize the delivery of electrical stimulation therapy to patient 105. For example, in some cases, it may be desirable to deliver sub-perception therapy to patient 105. In these cases, processing circuitry 210 may set therapy stimulation programs 214 such that stimulation generation circuitry 202 delivers informed pulses to patient 105 at below the perception threshold or according to some scaling factor (e.g., a gain) to the perception threshold determined from an ECAP signal elicited by a control pulse. In some examples, the distance between electrodes 232, 234 and the target tissue of spinal cord 120 changes according to patient posture, patient activity, patient movements, or lead migration over time. Additionally, the distance between electrodes 232, 234 and the target tissue of spinal cord 120 may briefly change due to any one of a cough, a sneeze, a Valsalva maneuver, or another transient patient movement. Any of these movements may affect a patient's perception of the electrical stimulation therapy delivered by IMD 200. As such, to maintain a consistent level of therapy, such as consistent sub-perception therapy, it may be beneficial for IMD 200 to periodically measure the stimulation level for at least one of the perception threshold or the detection threshold and update therapy stimulation programs 214 accordingly. For example, since stimulation parameter values that define informed pulses may be based on a perception threshold or a detection threshold, IMD 200 may periodically update the stimulation level for the perception threshold or detection threshold to maintain effective therapy.

In some examples, IMD 200 is configured to perform a sequence of perception threshold measurements in order to periodically determine and update the stimulation level that results in the perception threshold. The sequence of perception threshold measurements may be performed at a predetermined frequency. In some example, to perform a perception threshold measurement of the sequence of perception threshold measurements, stimulation generation circuitry 202 is configured to deliver a plurality of informed pulses, and deliver a plurality of control pulses, where the plurality of control pulses is interleaved with at least some informed pulses of the plurality of informed pulses. Sensing circuitry 206 is configured to detect a plurality of ECAP signals, where sensing circuitry 206 is configured to sense each ECAP of the plurality of ECAP signals after a control pulse of the plurality of control pulses and prior to a subsequent informed pulse of the plurality of informed pulses. Processing circuitry 210 is configured to detect the ECAP signals and determine, based on one or more detected ECAP signals, the stimulation level that results in the perception threshold, wherein the stimulation level corresponding to a first stimulation parameter and control stimulation generation circuitry 202 to deliver the electrical stimulation therapy to patient 105.

More specifically, to determine the stimulation level for the perception threshold, IMD 200 may be configured to deliver a set of stimulation pulses (e.g., control pulses if ECAP signals are not detectable from the informed pulses) of the plurality of stimulation pulses that start at a first pulse amplitude selected to be a fraction of the previous perception threshold, fraction of the previously used stimulation parameter value, or some other initial amplitude value. A first simulation pulse of the set of stimulation pulses is delivered by stimulation generation circuitry 202 at the initial amplitude, and then IMD 200 incrementally increases the amplitude of subsequent stimulation pulses by a predetermined amount. In one example, the perception threshold may be 10 microvolts (μV) which resulted from a stimulation amplitude of 4 milliamps (mA) (e.g., the first stimulation level). However, the previous stimulation amplitude used for the stimulation pulses may be set to 0.75 percent of the stimulation amplitude at the perception threshold. If the fraction of the stimulation amplitude is 0.5, and the predetermined amount is 0.1 mA, IMD 200 may deliver a first stimulation pulse at 1.5 mA, a second stimulation pulse at 1.6 mA, a third stimulation pulse at 1.7 mA, and so on until the increasing stimulation amplitude of a stimulation pulse results in the characteristic ECAP value reaching the perception threshold. In response to achieving the perception threshold, the corresponding stimulation level of the pulse that resulted in the perception threshold can be set to the new stimulation level which may be associated with the stimulation amplitude of that same pulse. The new stimulation amplitude for subsequent stimulation pulses may then be set to, or based on, some fraction of the new stimulation level.

Additionally, to determine the stimulation level for the perception threshold using control pulses, processing circuitry 210 is configured to detect at least one characteristic ECAP value of each ECAP signal of a set of ECAP signals received by processing circuitry 210 from sensing circuitry 206, where the set of ECAP signals are sensed after stimulation generation circuitry 202 delivers respective control pulses interleaved with the second set of informed pulses. In this manner, sensing circuitry 206 is configured to receive ECAP signals in-between at least some informed pulses of the second set of informed pulses. Processing circuitry 210 is configured to determine a stimulation level of the first pulse at which the resulting characteristic ECAP value achieves the perception threshold. This stimulation level may be associated with the perception threshold and stored in storage device 212 as a part of thresholds 218. The same stimulation level may thus be used to determine electrical stimulation therapy on patient 105. Processing circuitry 210 may determine a stimulation parameter value of the pulse that elicited the characteristic ECAP value and associate that stimulation parameter value with the perception threshold. Subsequently, processing circuitry 210 may store the stimulation parameter value that is associated with the perception threshold in storage device 212 as a part of thresholds 218. In some examples, the characteristic ECAP value may include one or more, or a combination of, a peak current amplitude, a peak voltage amplitude, a gradient, and an area under the ECAP.

It may be difficult to monitor ECAP signals in order to identify the stimulation level of the perception threshold using IMD 200. For example, patient 105 may be able to perceive informed pulses that are delivered below the detection threshold for ECAP signals. In other words, the detection threshold may, in some cases, be greater than the perception threshold. In these cases, processing circuitry 210 may not be able to pinpoint an accurate stimulation level for the perception threshold using ECAPs sensed by sensing circuitry 206 in response to informed pulses and/or control pulses delivered by stimulation generation circuitry 202. However, even if the detection threshold is greater than the perception threshold and processing circuitry 210 is not able to determine the perception threshold, IMD 200 may still be enabled to maintain sub-perception therapy delivery to patient 105. For example, in order to maintain sub-perception therapy, IMD 200 is configured to determine the stimulation level of the detection threshold and deliver informed pulses to patient 105 at a fraction of the stimulation level, where the fraction of the stimulation level of the detection threshold is below the perception threshold.

In some examples, to determine the stimulation level of the detection threshold, IMD 200 is configured to deliver a set of stimulation pulses (e.g., informed pulses, or control pulses when ECAP signals cannot be detected from informed pulses) using stimulation generation circuitry 202. Stimulation generation circuitry 202 is configured to deliver the plurality of stimulation pulses at a pulse amplitude value. Processing circuitry 210 is configured to determine whether an ECAP signal is detected after each stimulation pulse. In this manner, processing circuitry 210 is configured to determine if sensing circuitry 206 senses an ECAP corresponding to each stimulation pulse. Processing circuitry 210 is configured to determine how many ECAPs were detected for the total number of delivered stimulation pulses. IMD 200 can then compare this ratio of ECAP signals to total number of stimulation pulses to a desired threshold ratio (e.g., a ration between 25 percent and 75 percent, such as 4:7) to determine if the amplitude value is representative of the detection threshold of the detected ECAPs. In one example, if an ECAP is detected more often than not (e.g., greater than 50 percent of the time), but not all of the time (e.g., less than 90 percent of the time), then the amplitude value of those stimulation pulses may be associated with the detection threshold of those ECAP signals.

In response to determining that a ratio of the detected ECAP signals to the total number of stimulation signals is greater than a threshold ratio, processing circuitry 210 may instruct stimulation generation circuitry 202 to reduce the amplitude value of subsequent stimulation pulses. In response to determining that the ratio of the detected ECAP signals to the total number of stimulation signals is less than the threshold ratio, processing circuitry 210 may instruct stimulation generation circuitry 202 to increase the amplitude value of subsequent stimulation pulses. In some cases, processing circuitry 210 may determine that the ratio of the detected ECAP signals to the total number of stimulation signals is equal to the threshold ratio, or within an accepted range of the threshold ratio plus or minus an offset. In these cases, processing circuitry 210 may determine that the pulse amplitude value of the set of stimulation pulses is set appropriately to the stimulation level of the detection threshold. In some examples, the threshold ratio is greater than 0.25 and less than 0.75. The threshold ratio value may be saved in storage device 212 as a part of threshold detection parameters 220.

Although, in some examples, sensing circuitry 206 senses ECAP signals which occur in response to control pulses delivered according to ECAP test stimulation programs 216, in other examples, sensing circuitry 206 senses ECAP signals which occur in response to informed pulses delivered according to therapy stimulation programs 214. The techniques of this disclosure may enable IMD to detect the perception threshold and the detection threshold using any combination of ECAPs corresponding to informed pulses and ECAPs corresponding to control pulses.

Sensor(s) 222 may include one or more sensing elements that sense values of a respective patient parameter. As described, electrodes 232 and 234 may be the electrodes that sense the parameter value of the ECAP. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity, and processing circuitry 210 may increase the frequency of control pulses and ECAP sensing in response to detecting increased patient activity. In one example, processing circuitry 210 may initiate control pulses and corresponding ECAP sensing in response to a signal from sensor(s) 222 indicating that patient activity has exceeded an activity threshold. Conversely, processing circuitry 210 may decrease the frequency of control pulses and ECAP sensing in response to detecting decreased patient activity. For example, in response to sensor(s) 222 no longer indicating that the sensed patient activity exceeds a threshold, processing circuitry 210 may suspend or stop delivery of control pulses and ECAP sensing. In this manner, processing circuitry 210 may dynamically deliver control pulses and sense ECAP signals based on patient activity to reduce power consumption of the system when the electrode-to-neuron distance is not likely to change and increase system response to ECAP changes when electrode-to-neuron distance is likely to change. IMD 200 may include additional sensors within the housing of IMD 200 and/or coupled via one of leads 130 or other leads. In addition, IMD 200 may receive sensor signals wirelessly from remote sensors via telemetry circuitry 208, for example. In some examples, one or more of these remote sensors may be external to patient (e.g., carried on the external surface of the skin, attached to clothing, or otherwise positioned external to patient 105). In some examples, signals from sensor(s) 222 indicate a position or body state (e.g., sleeping, awake, sitting, standing, or the like), and processing circuitry 210 may select target ECAP characteristic values according to the indicated position or body state.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 3:
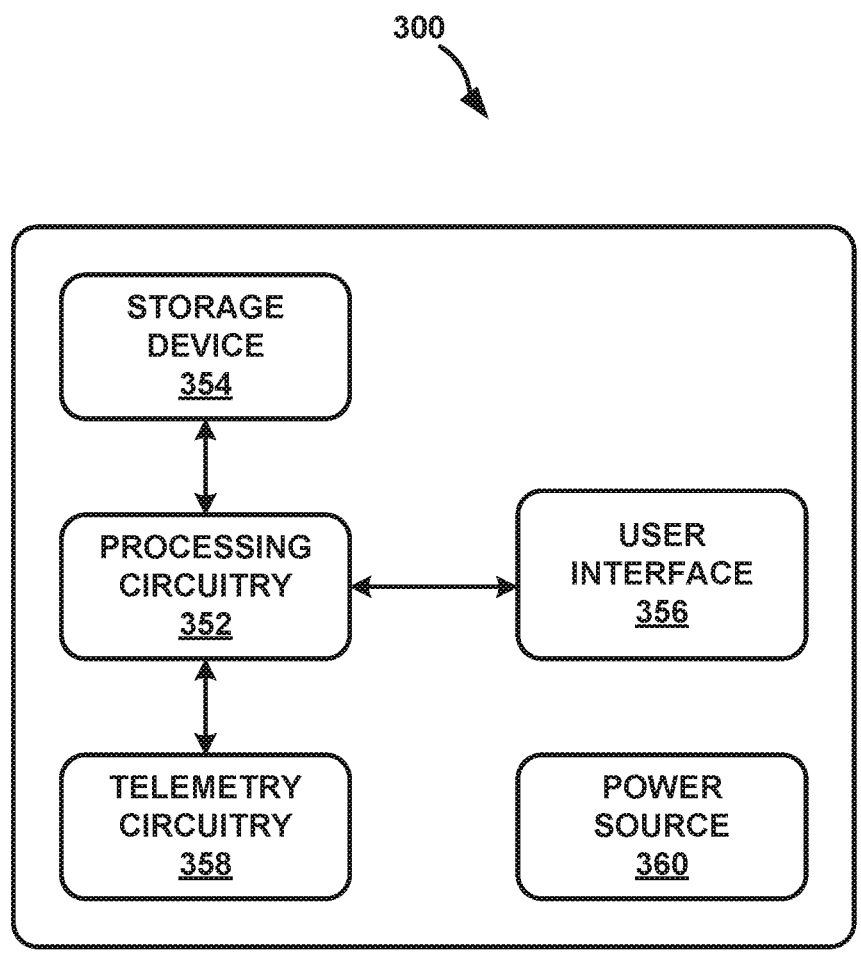
FIG. 3 is a block diagram illustrating an example configuration of components of an example external programmer, in accordance with one or more techniques of this disclosure.

FIG. 3 is a block diagram of the example external programmer 300. External programmer 300 may be an example of external programmer 150 of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include processing circuitry configured to perform the processes discussed with respect to processing circuitry 352.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory, select a spatial electrode movement pattern, or receive a user input and send a corresponding command to IMD 200, or instructions for any other functionality. In addition, storage device 354 may include a plurality of programs, where each program includes a parameter set that defines therapy stimulation or control stimulation. Storage device 354 may also store data received from a medical device (e.g., IMD 110). For example, storage device 354 may store ECAP related data recorded at a sensing module of the medical device, and storage device 354 may also store data from one or more sensors of the medical device.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation, identified patient behaviors, sensed patient parameter values, patient behavior criteria, or any other such information. User interface 356 may also receive user input (e.g., indication of when the patient perceives a stimulation pulse) via user interface 356. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 300 provides visual, audible, and/or tactile notifications that indicate there are new instructions. External programmer 300 requires receiving user input acknowledging that the instructions have been completed in some examples.

According to the techniques of the disclosure, user interface 356 of external programmer 300 receives an indication from a clinician instructing a processor of the medical device to update one or more therapy stimulation programs or to update one or more ECAP test stimulation programs. Updating therapy stimulation programs and ECAP test stimulation programs may include changing one or more parameters of the stimulation pulses delivered by the medical device according to the programs, such as amplitude, pulse width, frequency, and pulse shape of the informed pulses and/or control pulses. User interface 356 may also receive instructions from the clinician commanding any electrical stimulation, including therapy stimulation and control stimulation to commence or to cease.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
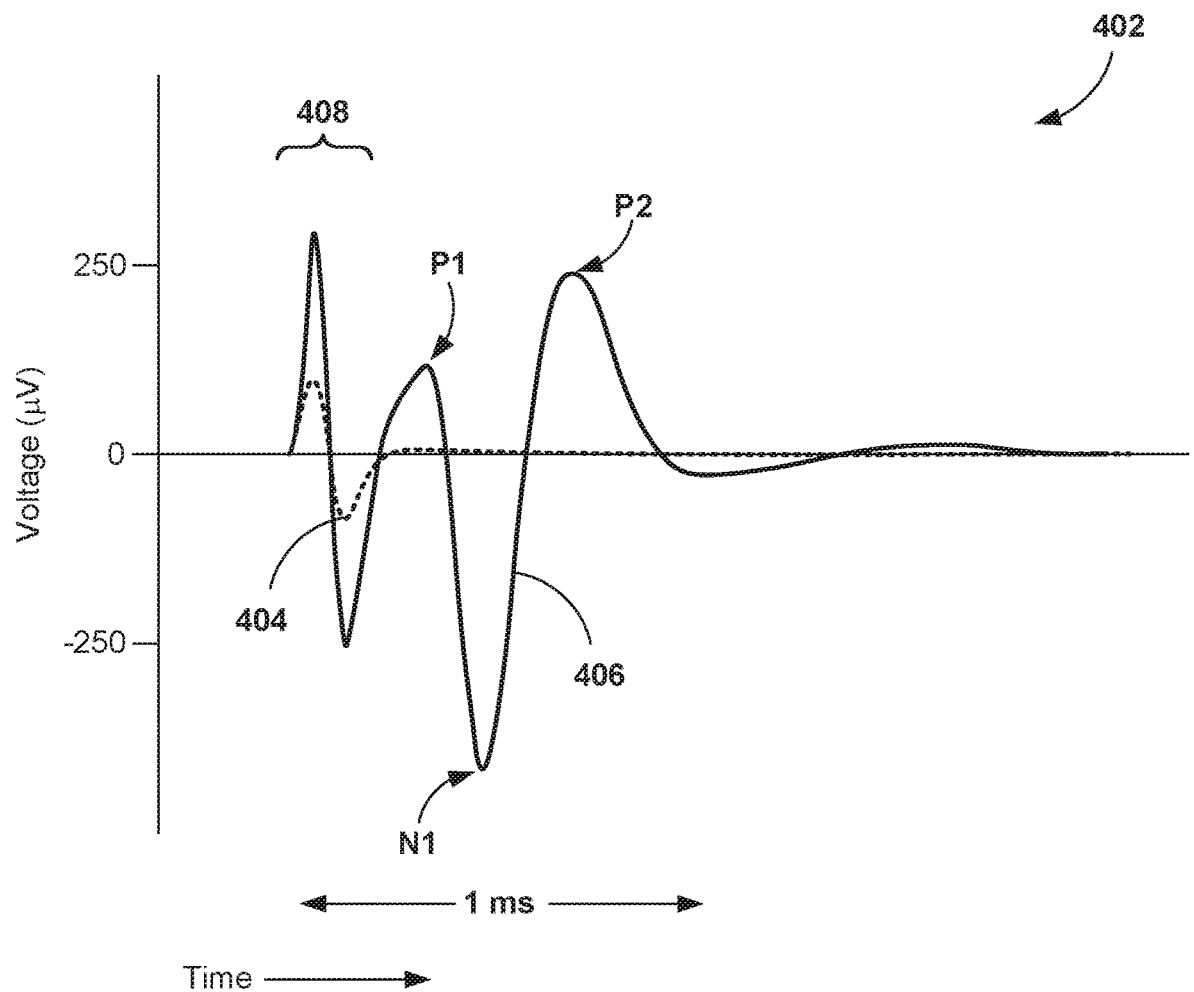
FIG. 4 is a graph of example evoked compound action potentials (ECAPs) sensed for respective stimulation pulses, in accordance with one or more techniques of this disclosure.

FIG. 4 is a graph 402 of example evoked compound action potentials (ECAP) signals sensed for respective stimulation pulses, in accordance with one or more techniques of this disclosure. As shown in FIG. 4, graph 402 shows example ECAP signal 404 (dotted line) and ECAP signal 406 (solid line). In some examples, each of ECAP signals 404 and 406 are sensed from control pulses that were delivered from a guarded cathode, where the control pulses are bi-phasic pulses including an interphase interval between each positive and negative phase of the pulse. In some such examples, the guarded cathode includes stimulation electrodes located at the end of an 8-electrode lead (e.g., leads 130 of FIG. 1) while two sensing electrodes are provided at the other end of the 8-electrode lead. ECAP signal 404 illustrates the voltage amplitude sensed as a result from a sub-detection threshold stimulation pulse. Peaks 408 of ECAP signal 404 are detected and represent the artifact of the delivered control pulse. However, no propagating signal is detected after the artifact in ECAP signal 404 because the control pulse was sub-detection threshold.

In contrast to ECAP signal 404, ECAP signal 406 represents the voltage amplitude detected from a supra-detection threshold control pulse. Peaks 408 of ECAP signal 406 are detected and represent the artifact of the delivered control pulse. After peaks 408, ECAP signal 406 also includes peaks P1, N1, and P2, which are three typical peaks representative of propagating action potentials from an ECAP. The example duration of the artifact and peaks P1, N1, and P2 is approximately 1 millisecond (ms). When detecting the ECAP of ECAP signal 406, different characteristics may be identified. For example, the characteristic of the ECAP may be the amplitude between N1 and P2. This N1-P2 amplitude may be easily detectable even if the artifact impinges on P1, a relatively large signal, and the N1-P2 amplitude may be minimally affected by electronic drift in the signal. In other examples, the characteristic of the ECAP used to control informed pulses may be an amplitude of P1, N1, or P2 with respect to neutral or zero voltage. In some examples, the characteristic of the ECAP used to control informed pulses is a sum of two or more of peaks P1, N1, or P2. In other examples, the characteristic of ECAP signal 406 may be the area under one or more of peaks P1, N1, and/or P2. In other examples, the characteristic of the ECAP may be a ratio of one of peaks P1, N1, or P2 to another one of the peaks. In some examples, the characteristic of the ECAP is a slope between two points in the ECAP signal, such as the slope between N1 and P2. In other examples, the characteristic of the ECAP may be the time between two points of the ECAP, such as the time between N1 and P2. The time between when the stimulation pulse is delivered and a point in the ECAP signal may be referred to as a latency of the ECAP and may indicate the types of fibers being captured by the stimulation pulse (e.g., a control pulse). ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Latency may also refer to the time between an electrical feature is detected at one electrode and then detected again at a different electrode. This time, or latency, is inversely proportional to the conduction velocity of the nerve fibers. Other characteristics of the ECAP signal may be used in other examples.

The amplitude of the ECAP signal increases with increased amplitude of the control pulse, as long as the pulse amplitude is greater than threshold such that nerves depolarize and propagate the signal. The target ECAP characteristic (e.g., the target ECAP amplitude) may be determined from the ECAP signal detected from a control pulse when informed pulses are determined to deliver effective therapy to patient 105. The ECAP signal thus is representative of the distance between the stimulation electrodes and the nerves appropriate for the stimulation parameter values of the informed pulses delivered at that time. Therefore, IMD 110 may attempt to use detected changes to the measured ECAP characteristic value to change informed pulse parameter values and maintain the target ECAP characteristic value during informed pulse delivery.

Figure 5A:
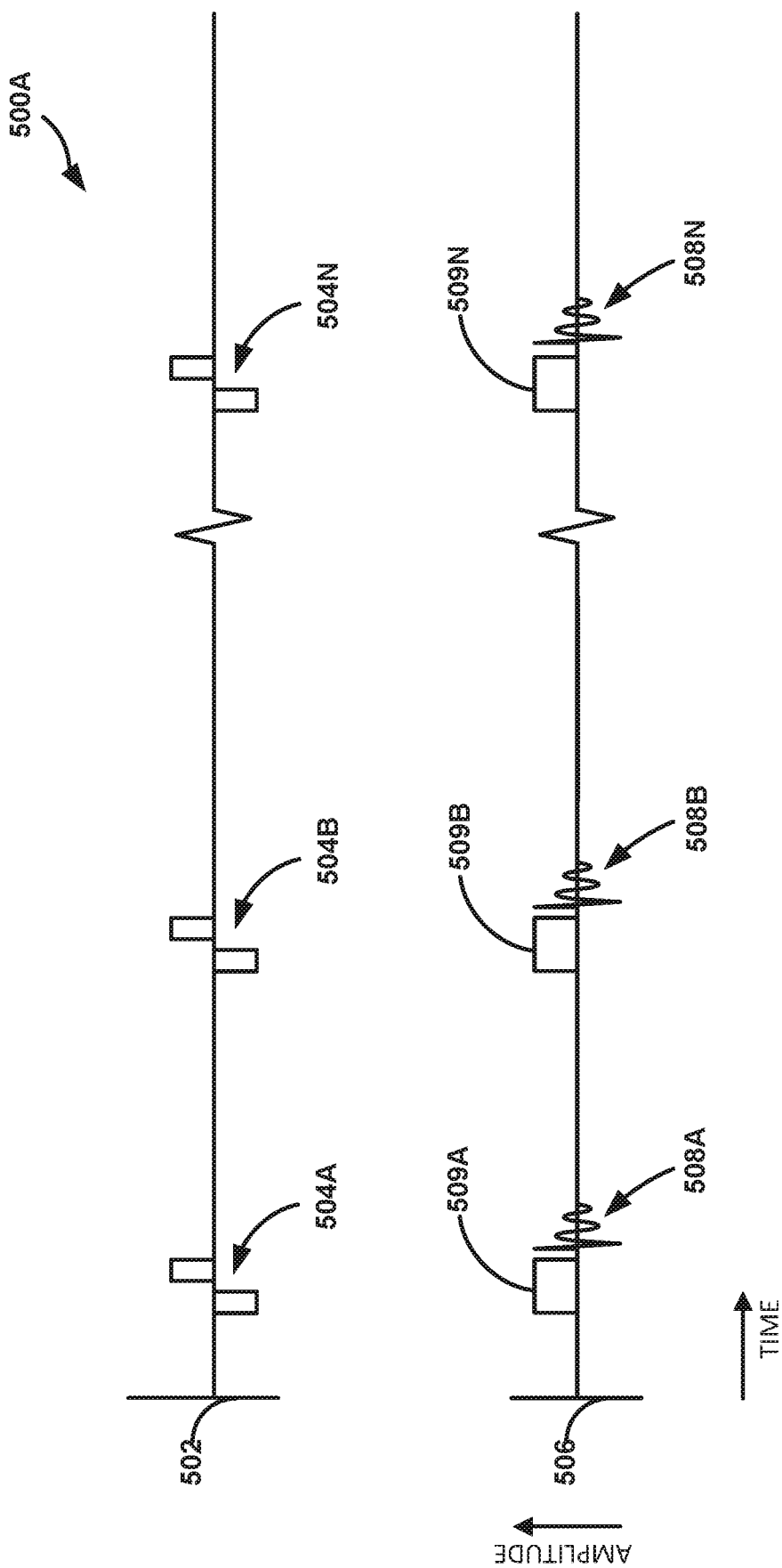
FIG. 5A is a timing diagram illustrating one example of electrical stimulation pulses and respective sensed ECAPs, in accordance with one or more techniques of this disclosure.

FIG. 5A is a timing diagram 500A illustrating an example of electrical stimulation pulses and respective sensed ECAPs, in accordance with one or more techniques of this disclosure. For convenience, FIG. 5A is described with reference to IMD 200 of FIG. 2. As illustrated, timing diagram 500A includes first channel 502, a plurality of control pulses 504A-504N (collectively "control pulses 504"), second channel 506, a plurality of respective ECAPs 508A-508N (collectively "ECAPs 508"), and a plurality of stimulation interference signals 509A-509N (collectively "stimulation interference signals 509"). In the example of FIG. 5A, IMD 200 can deliver therapy with control pulses instead of informed pulses.

First channel 502 is a time/voltage (and/or current) graph indicating the voltage (or current) of at least one electrode of electrodes 232, 234. In one example, the stimulation electrodes of first channel 502 may be located on the opposite side of the lead as the sensing electrodes of second channel 506. Control pulses 504 may be electrical pulses delivered to the spinal cord of the patient by at least one of electrodes 232, 234, and control pulses 504 may be balanced biphasic square pulses with an interphase interval. In other words, each of control pulses 504 are shown with a negative phase and a positive phase separated by an interphase interval. For example, a control pulse 504 may have a negative voltage for the same amount of time and amplitude that it has a positive voltage. It is noted that the negative voltage phase may be before or after the positive voltage phase. Control pulses 504 may be delivered according to ECAP test stimulation programs 216 stored in storage device 212 of IMD 200, and ECAP test stimulation programs 216 may be updated according to user input via an external programmer and/or may be updated according to a signal from sensor(s) 222. In one example, control pulses 504 may have a pulse width of less than approximately 300 microseconds (e.g., the total time of the positive phase, the negative phase, and the interphase interval is less than 300 microseconds). In another example, control pulses 504 may have a pulse width of approximately 100 μs for each phase of the bi-phasic pulse. As illustrated in FIG. 5A, control pulses 504 may be delivered via channel 502. Delivery of control pulses 504 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 506 is a time/voltage (and/or current) graph indicating the voltage (or current) of at least one electrode of electrodes 232, 234. In one example, the electrodes of second channel 506 may be located on the opposite side of the lead as the electrodes of first channel 502. ECAPs 508 may be sensed at electrodes 232, 234 from the spinal cord of the patient in response to control pulses 504. ECAPs 508 are electrical signals which may propagate along a nerve away from the origination of control pulses 504. In one example, ECAPs 508 are sensed by different electrodes than the electrodes used to deliver control pulses 504. As illustrated in FIG. 5A, ECAPs 508 may be recorded on second channel 506.

Stimulation interference signals 509A, 509B, and 509N (e.g., the artifact of the stimulation pulses) may be sensed by leads 230 and may be sensed during the same period of time as the delivery of control pulses 504. Since the interference signals may have a greater amplitude and intensity than ECAPs 508, any ECAPs arriving at IMD 200 during the occurrence of stimulation interference signals 509 may not be adequately sensed by sensing circuitry 206 of IMD 200. However, ECAPs 508 may be sufficiently sensed by sensing circuitry 206 because each ECAP 508, or at least a portion of ECAP 508 used as feedback for control pulses 504, falls after the completion of each a control pulse 504. As illustrated in FIG. 5A, stimulation interference signals 509 and ECAPs 508 may be recorded on channel 506.

Figure 5B:
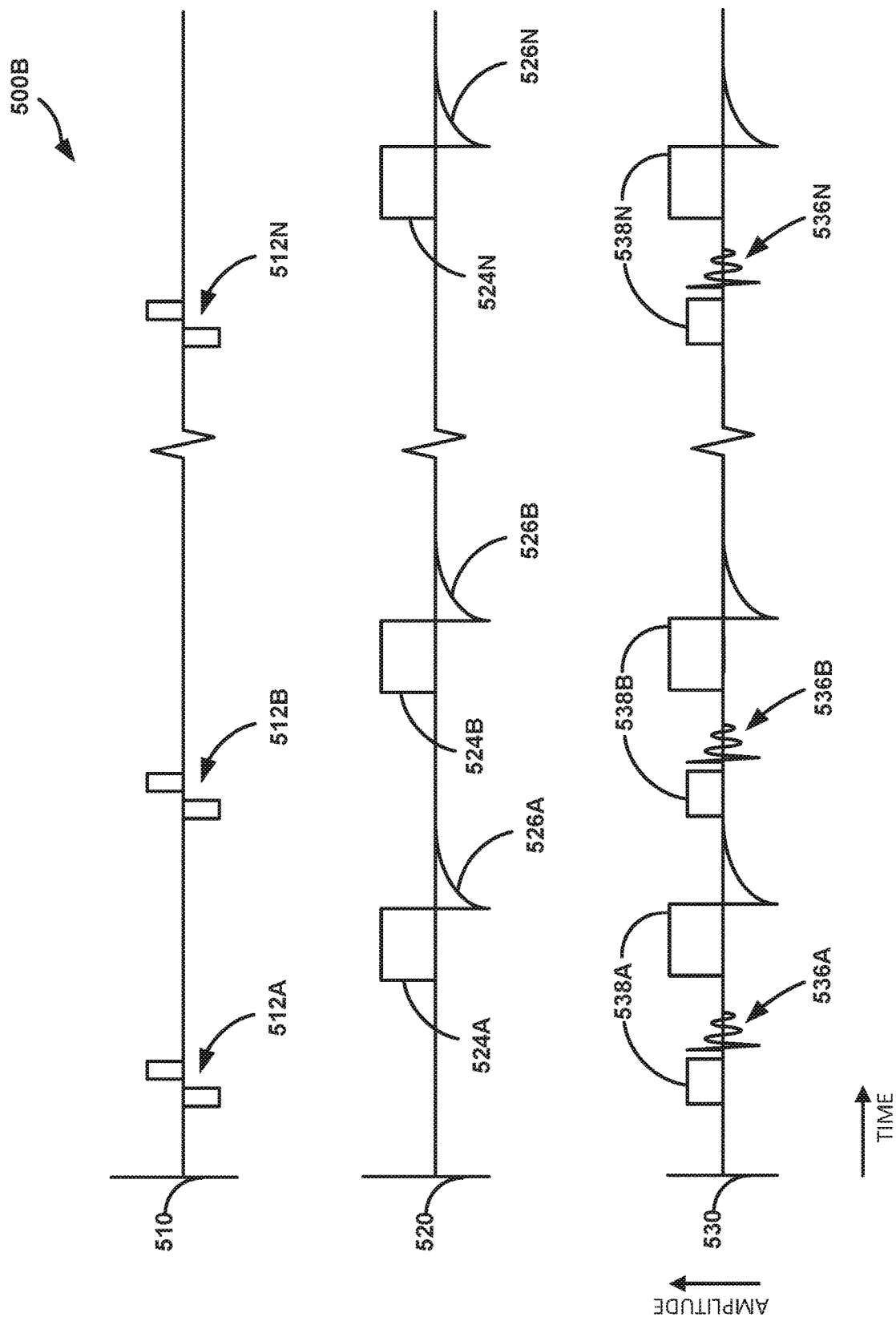
FIG. 5B is a timing diagram illustrating another example of electrical stimulation pulses and respective sensed ECAPs, in accordance with one or more techniques of this disclosure.

FIG. 5B is a timing diagram 500B illustrating another example of electrical stimulation pulses and respective sensed ECAPs, in accordance with one or more techniques of this disclosure. For convenience, FIG. 5B is described with reference to IMD 200 of FIG. 2. As illustrated, timing diagram 500B includes first channel 510, a plurality of control pulses 512A-512N (collectively "control pulses 512"), second channel 520, a plurality of informed pulses 524A-524N (collectively "informed pulses 524") including passive recharge phases 526A-526N (collectively "passive recharge phases 526"), third channel 530, a plurality of respective ECAPs 536A-536N (collectively "ECAPs 536"), and a plurality of stimulation interference signals 538A-538N (collectively "stimulation interference signals 538").

First channel 510 is a time/voltage (and/or current) graph indicating the voltage (or current) of at least one electrode of electrodes 232, 234. In one example, the stimulation electrodes of first channel 510 may be located on the opposite side of the lead as the sensing electrodes of third channel 530. Control pulses 512 may be electrical pulses delivered to the spinal cord of the patient by at least one of electrodes 232, 234, and control pulses 512 may be balanced biphasic square pulses with an interphase interval. In other words, each of control pulses 512 are shown with a negative phase and a positive phase separated by an interphase interval. For example, a control pulse 512 may have a negative voltage for the same amount of time and amplitude that it has a positive voltage. It is noted that the negative voltage phase may be before or after the positive voltage phase. Control pulses 512 may be delivered according to ECAP test stimulation programs 216 stored in storage device 212 of IMD 200, and ECAP test stimulation programs 216 may be updated according to user input via an external programmer and/or may be updated according to a signal from sensor(s) 222. In one example, control pulses 512 may have a pulse width of less than approximately 300 microseconds (e.g., the total time of the positive phase, the negative phase, and the interphase interval is less than 300 microseconds). In another example, control pulses 512 may have a pulse width of approximately 100 μs for each phase of the bi-phasic pulse. As illustrated in FIG. 5B, control pulses 512 may be delivered via channel 510. Delivery of control pulses 512 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 520 is a time/voltage (and/or current) graph indicating the voltage (or current) of at least one electrode of electrodes 232, 234 for the informed pulses. In one example, the electrodes of second channel 520 may partially or fully share common electrodes with the electrodes of first channel 510 and third channel 530. Informed pulses 524 may also be delivered by the same leads 230 that are configured to deliver control pulses 512. Informed pulses 524 may be interleaved with control pulses 512, such that the two types of pulses are not delivered during overlapping periods of time. However, informed pulses 524 may or may not be delivered by exactly the same electrodes that deliver control pulses 512. Informed pulses 524 may be monophasic pulses with pulse widths of greater than approximately 300 μs and less than approximately 1200 μs. In fact, informed pulses 524 may be configured to have longer pulse widths than control pulses 512. As illustrated in FIG. 5B, informed pulses 524 may be delivered on channel 520.

Informed pulses 524 may be configured for passive recharge. For example, each informed pulse 524 may be followed by a passive recharge phase 526 to equalize charge on the stimulation electrodes. Unlike a pulse configured for active recharge, wherein remaining charge on the tissue following a stimulation pulse is instantly removed from the tissue by an opposite applied charge, passive recharge allows tissue to naturally discharge to some reference voltage (e.g., ground or a rail voltage) following the termination of the informed pulse. In some examples, the electrodes of the medical device may be grounded at the medical device body. In this case, following the termination of informed pulse 524, the charge on the tissue surrounding the electrodes may dissipate to the medical device, creating a rapid decay of the remaining charge at the tissue following the termination of the pulse. This rapid decay is illustrated in passive recharge phases 526. Passive recharge phase 526 may have a duration in addition to the pulse width of the preceding informed pulse 524. In other examples (not pictured in FIG. 5B), informed pulses 524 may be bi-phasic pulses having a positive and negative phase (and, in some examples, an interphase interval between each phase) which may be referred to as pulses including active recharge. A informed pulse that is a bi-phasic pulse may or may not have a following passive recharge phase.

Third channel 530 is a time/voltage (and/or current) graph indicating the voltage (or current) of at least one electrode of electrodes 232, 234. In one example, the electrodes of third channel 530 may be located on the opposite side of the lead as the electrodes of first channel 510. ECAPs 536 may be sensed at electrodes 232, 234 from the spinal cord of the patient in response to control pulses 512. ECAPs 536 are electrical signals which may propagate along a nerve away from the origination of control pulses 512. In one example, ECAPs 536 are sensed by different electrodes than the electrodes used to deliver control pulses 512. As illustrated in FIG. 5B, ECAPs 536 may be recorded on third channel 530.

Stimulation interference signals 538A, 538B, and 538N (e.g., the artifact of the stimulation pulses) may be sensed by leads 230 and may be sensed during the same period of time as the delivery of control pulses 512 and informed pulses 524. Since the interference signals may have a greater amplitude and intensity than ECAPs 536, any ECAPs arriving at IMD 200 during the occurrence of stimulation interference signals 538 may not be adequately sensed by sensing circuitry 206 of IMD 200. However, ECAPs 536 may be sufficiently sensed by sensing circuitry 206 because each ECAP 536 falls after the completion of each a control pulse 512 and before the delivery of the next informed pulse 524. As illustrated in FIG. 5B, stimulation interference signals 538 and ECAPs 536 may be recorded on channel 530.

Figure 6:
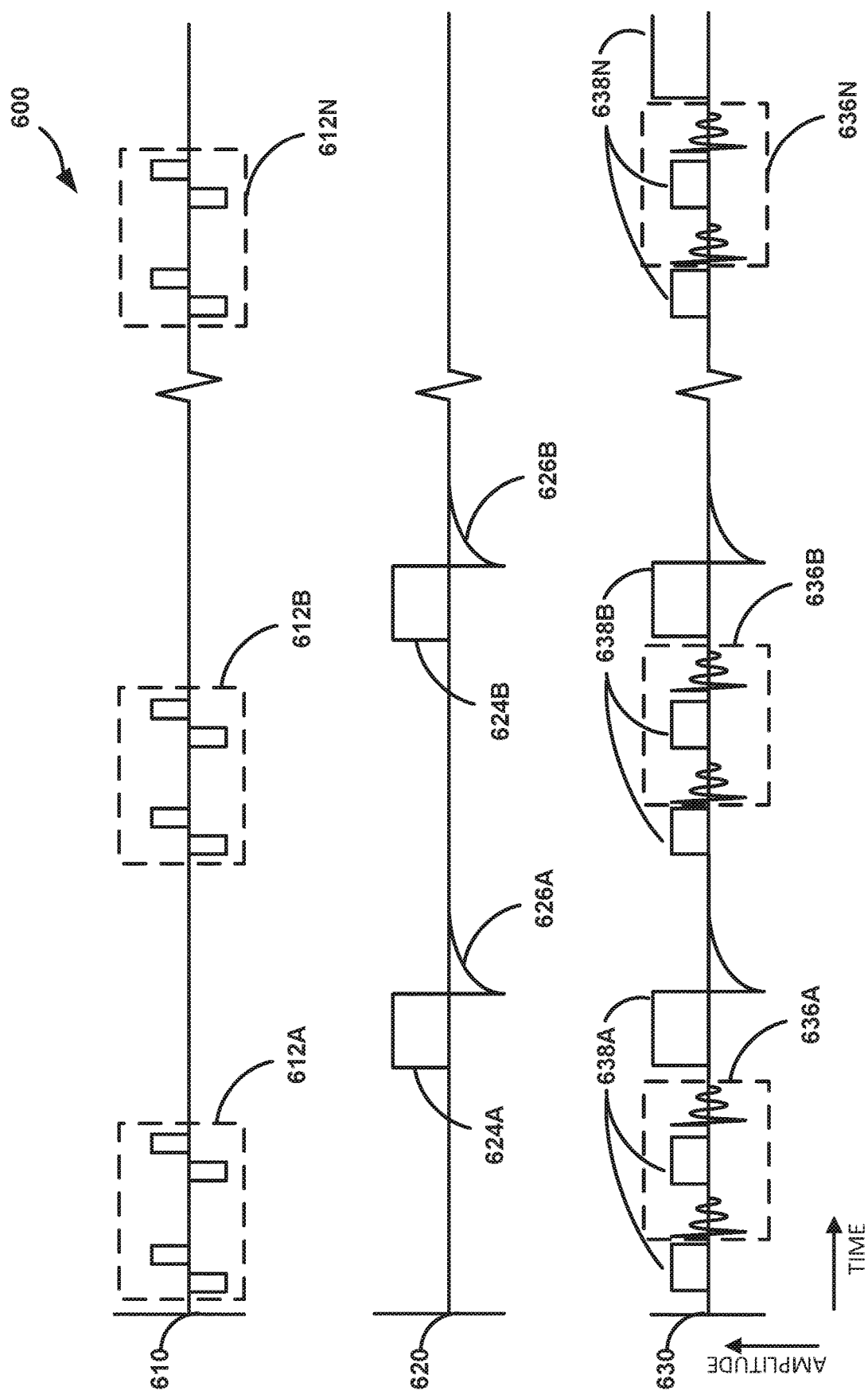
FIG. 6 is a timing diagram illustrating another example of electrical stimulation pulses and respective ECAPs, in accordance with one or more techniques of this disclosure.

FIG. 6 is a timing diagram 600 illustrating another example of electrical stimulation pulses and respective ECAPs, in accordance with one or more techniques of this disclosure. For convenience, FIG. 6 is described with reference to IMD 200 of FIG. 2. As illustrated, timing diagram 600 includes first channel 610, a plurality of control pulses 612A-612N (collectively "control pulses 612"), second channel 620, a plurality of informed pulses 624A-624N (collectively "informed pulses 624") including passive recharge phases 626A-626N (collectively "passive recharge phases 626"), third channel 630, a plurality of respective ECAPs 636A-636N (collectively "ECAPs 636"), and a plurality of stimulation interference signals 638A-638N (collectively "stimulation interference signals 638"). FIG. 6 may be substantially similar to FIG. 5B, except for the differences detailed below.

Two or more (e.g. two) control pulses 612 may be delivered during each time event (e.g., window) of a plurality of time events, and each time event represents a time between two consecutive informed pulses 624. For example, during each time event, a first control pulse may be directly followed by a first respective ECAP, and subsequent to the completion of the first respective ECAP, a second control pulse may be directly followed by a second respective ECAP. Informed pulses may commence following the second respective ECAP. In other examples not illustrated here, three or more control pulses 612 may be delivered, and respective ECAP signals sensed, during each time event of the plurality of time events.

Figure 7:
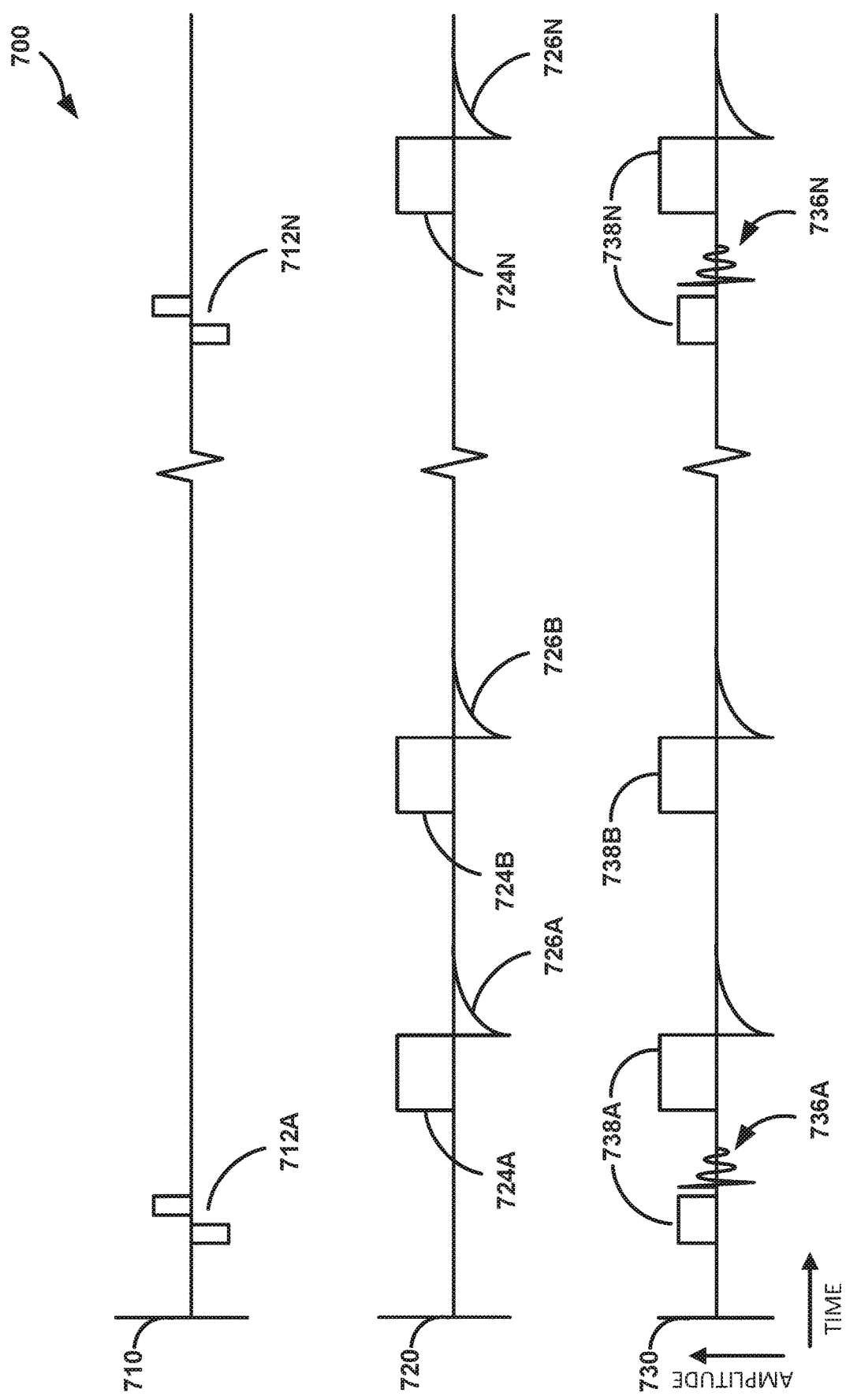
FIG. 7 is a timing diagram illustrating another example of electrical stimulation pulses and respective ECAPs, in accordance with one or more techniques of this disclosure.

FIG. 7 is a timing diagram 700 illustrating another example of electrical stimulation pulses and respective ECAPs, in accordance with one or more techniques of this disclosure. For convenience, FIG. 7 is described with reference to IMD 200 of FIG. 2. As illustrated, timing diagram 700 includes first channel 710, a plurality of control pulses 712A-712N (collectively "control pulses 712"), second channel 720, a plurality of informed pulses 724A-724N (collectively "informed pulses 724") including passive recharge phases 726A-726N (collectively "passive recharge phases 726"), third channel 730, a plurality of respective ECAPs 736A-736N (collectively "ECAPs 736"), and a plurality of stimulation interference signals 738A-738N (collectively "stimulation interference signals 738"). FIG. 7 may be substantially similar to FIG. 5B, except for the differences detailed below.

In previous examples illustrated in FIG. 5B and FIG. 6, at least one control pulse was delivered and interleaved between each pair of consecutive informed pulses. However, in some examples, control pulses 712 are not delivered during each time event (or window) of the plurality of time events, wherein each time event represents a time between two consecutive informed pulses 724. As illustrated in the example of FIG. 7, a control pulse 712 is not delivered following informed pulse 724A and preceding informed pulse 724B. In other words, consecutive informed pulses 724A and 724B may be delivered without an intervening control pulse. In any case, informed pulses are delivered according to a predetermined frequency, and control pulses may be delivered at any time between the informed pulses.

Control pulses may be administered according to ECAP test stimulation programs 216. Processing circuitry 210 may be configured to update ECAP test stimulation programs according to user input via telemetry circuitry 208, and also by a signal from sensor(s) 222. For example, a clinician may operate a patient programmer and send a signal to telemetry circuitry 208 including instructions for updating ECAP test stimulation programs 216. The clinician may set control stimulation to any of the examples illustrated in FIGS. 5-7, and the clinician also may customize control stimulation to a configuration not illustrated in FIGS. 5-7. The clinician may elect to cease control stimulation or commence control stimulation at any time. In some examples, a detection that the patient's posture or activity level has changed will initiate control stimulation. As described herein, stimulation levels for a stimulation threshold (e.g., a perception threshold and/or a detection threshold) may be determined by ECAP signals detected from control pulses as shown in FIGS. 5-7, and one or more stimulation parameter values that defines informed pulses may be determined based on the determined stimulation level of the stimulation threshold. For example, processing circuitry 210 may determine the stimulation parameter values directly from the stimulation level or based on a stimulation parameter value defining control pulses and selected from the stimulation level (e.g., a gain value applied to the stimulation parameter value for the control pulses).

Figure 8:
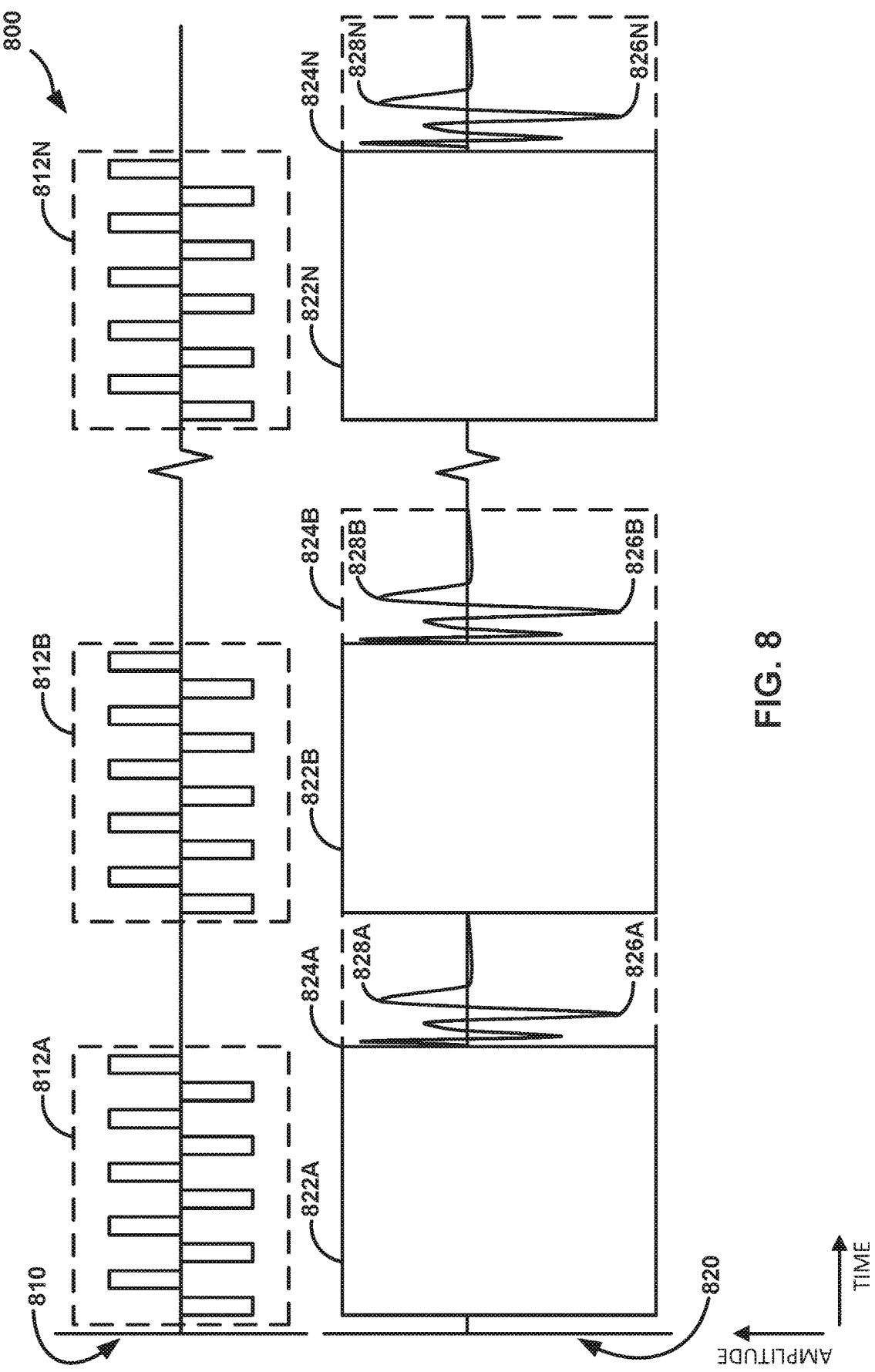
FIG. 8 is a timing diagram illustrating another example of electrical stimulation pulses and respective sensed ECAPs, in accordance with one or more techniques of this disclosure.

FIG. 8 is a timing diagram 800 illustrating another example of electrical stimulation pulses and respective sensed ECAP signals, in accordance with one or more techniques of this disclosure. For convenience, FIG. 8 is described with reference to IMD 200 of FIG. 2. As illustrated, timing diagram 800 includes first channel 810, a plurality of informed pulse bursts 812A-812N (collectively, "informed pulse bursts 812"), second channel 820, a plurality of sensed artifacts 822A-822N (collectively, "sensed artifacts 822"), a plurality of respective ECAPs 824A-824N (collectively "ECAPs 824"), a plurality of N1 ECAP peaks 826A-826N (collectively, "N1 ECAP peaks 826"), and a plurality of P2 ECAP peaks 828A-828N (collectively, "P2 ECAP peaks 828").

First channel 810 is a time/voltage (and/or current) graph indicating the voltage (or current) of at least one electrode of electrodes 232, 234. In some examples, first channel 810 may represent the voltage of at least one stimulation electrode of electrodes 232, 234 that delivers the plurality of informed pulse bursts 812. In the example of FIG. 8, each informed pulse burst of the plurality of informed pulse bursts 812 includes five informed pulses. Alternatively, in other examples, each informed pulse burst of the plurality of informed pulse bursts 812 may include greater than five informed pulses or less than five informed pulses. In one example, the stimulation electrodes that deliver the bursts of informed pulses 812 may be located on the opposite side of leads 230 as sensing electrodes which record the signals of second channel 820. The informed pulses of informed pulse bursts 812 may be balanced biphasic square pulses with an interphase interval. In other words, each informed pulse of informed pulse bursts 812 are shown with a negative phase and a positive phase separated by an interphase interval. For example, informed pulse may have a negative voltage for the same amount of time and amplitude that it has a positive voltage. It is noted that the negative voltage phase may be before or after the positive voltage phase.

Informed pulse bursts 812 may be delivered according to therapy stimulation programs 214 stored in storage device 212 of IMD 200, and therapy stimulation programs 214 may be updated according to user input via an external programmer and/or may be updated according to a signal from sensor(s) 222. In one example, each informed pulse of informed pulse bursts 812 may have a pulse width of less than approximately 400 microseconds (e.g., the total time of the positive phase, the negative phase, and the interphase interval is less than 400 microseconds). In another example, each informed pulse of informed pulse bursts 812 may have a pulse width of approximately 150 µs for each phase of the bi-phasic pulse. In some examples, a frequency of the informed pulses within each informed pulse bursts 812 may be greater than 500 Hertz (Hz) and less than 1500 Hz. In other examples, the frequency of the informed pulses within each burst may be greater than 1500 Hz. As illustrated in FIG. 8, Informed pulse bursts 812 may be delivered via first channel 810. Delivery of informed pulse bursts 812 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 820 is a time/voltage (and/or current) graph indicating the voltage (or current) of at least one electrode of electrodes 232, 234. In one example, the electrodes of second channel 820 may be located on the opposite side of the lead as the electrodes of first channel 810. In the example of FIG. 8, second channel 820 is a sensing channel of leads 230. In this manner, second channel 820 is configured to record sensed artifacts 822A, 822B, and 822N (collectively "sensed artifacts 822") and ECAPs 824A, 824B, and 824N (collectively "ECAPs 824"). In some examples, the frequency of each informed pulse burst of informed pulse bursts 812 is high enough that channel 820 is not able to sense a fully or nearly fully manifested ECAP following each informed pulse of informed pulse bursts 812 because the next pulse in the burst overlaps the ECAP signal in time. However, following each informed pulse burst of informed pulse bursts 812 (e.g., during a pause in delivery of the informed pulse burst), second channel 820 may sense a respective ECAP of ECAPs 824. Since first channel 810 may not, in some cases, apply any stimulation for a period of time following each informed pulse burst, channel 820 may sense ECAPs 824 including N1 ECAP peaks 826 and P2 ECAP peaks 828 during the period of time following each of informed pulse bursts 812. To determine an ECAP amplitude for each of ECAPs 824, in some examples, IMD 200 determines a difference between an amplitude of a respective N1 peak and a respective P2 peak. For example, IMD 200 may determine that the amplitude of ECAP 824A is the difference between an amplitude of N1 peak 826A and an amplitude P2 peak 828A. By delivering informed pulses as illustrated in FIG. 8, IMD 200 may deliver high-frequency therapy stimulation to patient 105 while still recording ECAPs which may be used to determine therapy. In some examples, patient 105 may not perceive the "breaks" that occur following each of informed pulse bursts 812. Rather, in some such examples, patient 105 may perceive continuous high-frequency stimulation. In other examples, although the patient 105 may perceive a break between informed pulse bursts 812, that perceived break may not significantly reduce therapy efficacy.

In some examples, all of the stimulation pulses within a single pulse burst 812 may be the same (e.g., defined by the same stimulation parameters). In other examples, the last pulse in the pulse burst may be different from the previous pulses in order improve a resulting ECAP signal that is elicited and/or provide a pulse that does not interfere with ECAP detection. For example, the last pulse in each burst of pulses (or some bursts of pulses) may have one or more different stimulation parameter values, such as a different amplitude, pulse width, pulse shape, or other characteristic. In one example, the last pulse in each pulse burst 812 may have a larger amplitude than the other pulses in the same pulse burst. The last pulse may have a longer or shorter pulse width. In some examples, a shorter pulse width may reduce the likelihood of creating artifacts on the detected ECAP. In any case, the last pulse may have a larger or smaller charge or phase than other pulses in the same pulse burst, and the last pulse may be referred to as a control pulse. Earlier pulses in the same pulse burst may be referred to as informed pulses because they are informed by an ECAP elicited by a previous control pulse (e.g., the last pulse of a previous pulse burst).

Sensed artifacts 822 (e.g., the artifacts of the informed pulses) may be sensed by leads 230 and may be sensed during the same period of time as the delivery of informed pulse bursts 812. Since the interference signals may have a greater amplitude and intensity than ECAPs 824, any ECAPs arriving at IMD 200 during the occurrence of sensed artifacts 822 may not be adequately sensed by sensing circuitry 206 of IMD 200. However, ECAPs 824 may be sufficiently sensed by sensing circuitry 206 because each ECAP of ECAPs 824 falls near the completion or after the completion of each informed pulse burst 812 and before the delivery of the subsequent informed pulse burst 812. As illustrated in FIG. 8, sensed artifacts 822 and ECAPs 824 may be recorded on second channel 820.

Figure 9:
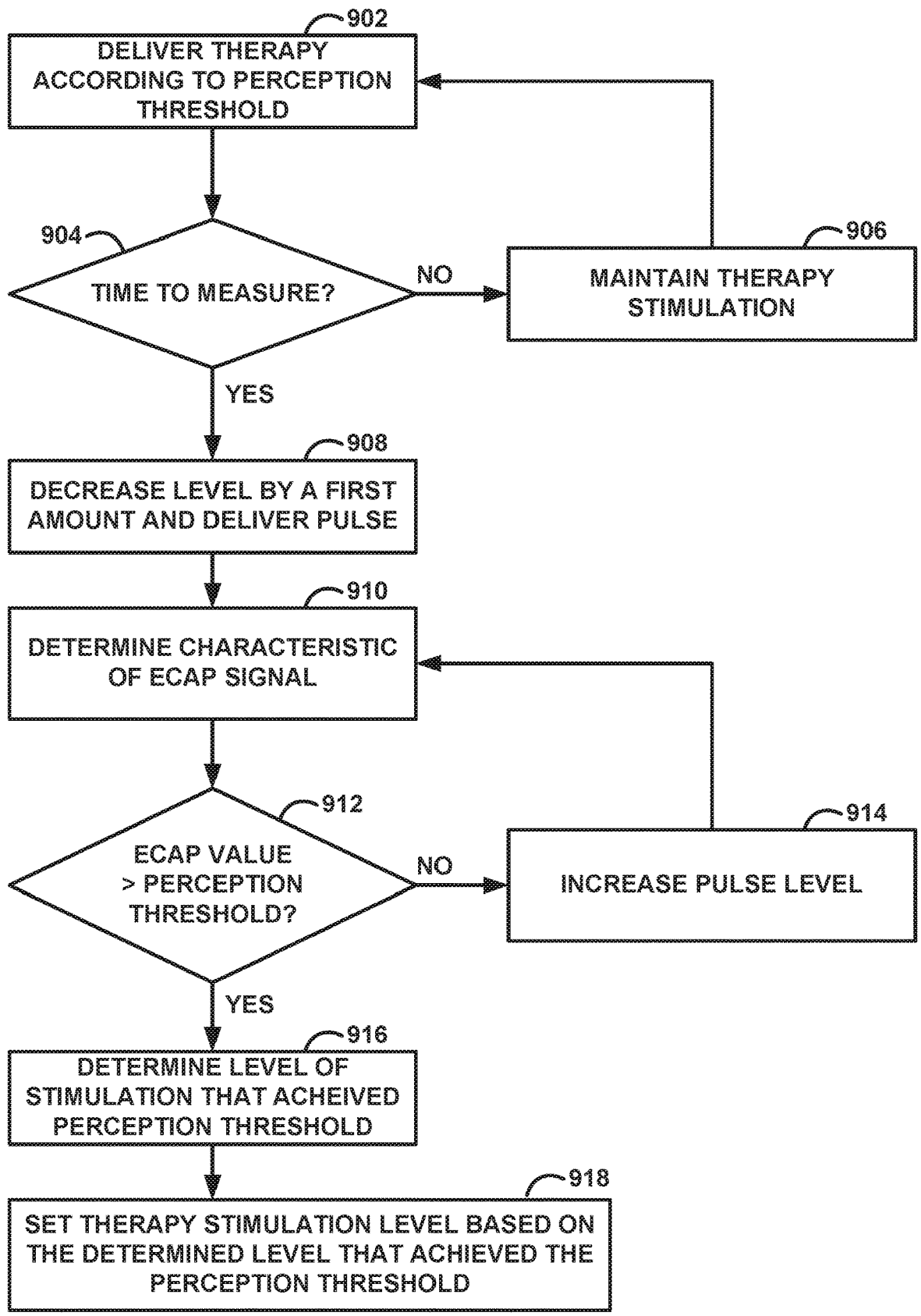
FIG. 9 is a flow diagram illustrating an example operation for determining a stimulation parameter according to a perception threshold, in accordance with one or more techniques of this disclosure.

FIG. 9 is a flow diagram illustrating an example operation for determining a stimulation level based on a perception threshold, in accordance with one or more techniques of this disclosure. For convenience, FIG. 9 is described with respect to IMD 200 of FIG. 2. However, the techniques of FIG. 9 may be performed by different components of IMD 200 or by additional or alternative medical devices.

IMD 200 may deliver stimulation therapy to a patient (e.g., patient 105). In some cases, IMD 200 delivers the stimulation therapy based on a perception threshold. The perception threshold may be associated with one or more parameter values (e.g., a stimulation level) that at least partially define the stimulation pulses in which a patient 105 is able to perceive the stimulation pulses. For example, patient 105 may not be able to perceive stimulation pulses delivered at a first pulse amplitude that is below the informed pulse level associated with the perception threshold. However, patient 105 may be able to perceive informed pulses delivered at a pulse amplitude (and/or pulse width or pulse frequency) greater than the pulse amplitude associated with the perception threshold. In this manner, stimulation pulses may be delivered at, or below, the pulse amplitude and/or other stimulation parameter level associated with the perception threshold. In order to maintain a consistent level of therapy delivered by IMD 200, It may be beneficial to periodically determine what stimulation level (e.g., pulse amplitude or pulse width) results in detection of a characteristic ECAP value at the perception threshold. In some cases, the actual perception threshold may be re-determined as well. FIG. 9 will be described as an example system that uses control pulses to detect ECAP signals and determine pulse amplitudes that result in characteristic ECAP values at the perception threshold. The stimulation parameter values of informed pulses may be selected directly from the control pulse levels that achieve the perception threshold or scaled as needed since the control pulses and informed pulses may provide different levels of perceived intensity. In other examples where ECAP signals are detectable from informed pulses, a similar technique may be used to FIG. 9 which replaces the control pulses with the informed pulses. In some cases, the control pulses elicit ECAPs that may be analyzed by IMD 200 to determine one or more characteristics of future control pulses and/or informed pulses delivered by IMD 200.

As illustrated in the example of FIG. 9, processing circuitry 210 of IMD 200 delivers informed pulses according to a previously determined stimulation parameter value from the perception threshold (902). For example, the perception threshold may be a characteristic ECAP value of approximately 10 mV elicited by a control pulse with a 4 mA current amplitude (e.g., a stimulation level). If IMD 200 is to deliver informed pulses with an amplitude 75% of the control pulse amplitude that achieved the characteristic ECAP value of the perception threshold, IMD 200 may deliver informed pulses having a 3 mA current amplitude. IMD 200 then determines if it is time to re-measure, or determine, the control pulse level that achieves the known perception threshold (904). IMD 200 may follow a perception threshold measurement frequency that represents a rate in which IMD 200 re-determines the control pulse level that achieves the perception threshold. The measurement frequency may include any frequency value or range of frequency values. In some cases, the measurement frequency may be one measurement per hour. In other cases, the measurement frequency may be two measurements per hour. In other cases, the measurement frequency may be sixty measurements per hour or even continuously. Alternatively, IMD 200 may update the control pulse level for the perception threshold in response to sensor 222 detecting a change in patient posture or activity. IMD 200 may receive instructions from external programmer 150 via telemetry circuitry 208 which set the measurement frequency. Additionally, IMD 200 may receive instructions from external programmer 150 which command processing circuitry 210 to update the measurement frequency.

If it is not time to perform a measurement ("NO" branch of block 904), IMD 200 maintains the therapy stimulation (906) delivered to patient 105. If it is time to perform a measurement ("YES" branch of block 904), processing circuitry 210 of IMD 200 decreases the amplitude of the control pulses by a first amount (908). Put another way, before the measurement, IMD 200 delivers the control pulses at a first level, and when the measurement begins, IMD 200 delivers the control pulses at a second level which is lower than the first level. The control pulses may still be interleaved with the informed pulses while this process continues. The "level" in which IMD 200 delivers control pulses may, in some cases, be dependent on a set of parameters values which may include one or more of amplitude, pulse width, or pulse frequency. As such, when IMD 200 decreases the control pulse level by the first amount, IMD 200 decreases at least one stimulation parameter value by the first amount. In some examples, IMD 200 decreases the pulse amplitude by the first amount. In other examples, IMD 200 decreases both of the pulse amplitude and the pulse width, where the collective decrease of the pulse amplitude and the pulse width defines the first amount.

After decreasing the therapy stimulation by the first amount, processing circuitry 210 delivers the control pulse and determines a characteristic ECAP value from the ECAP signal (910). In some examples, ECAP signal is directly elicited by a control pulse delivered by IMD 200 after processing circuitry decreases the level (e.g., amplitude) of the control pulses. The characteristic ECAP value may include an ECAP amplitude (e.g., P1 amplitude, N1 amplitude, P2 amplitude, or any combination thereof), an ECAP duration, an ECAP slope, or an area under one or more curves of the ECAP.

At block 912, processing circuitry determines if the characteristic ECAP value is greater than the perception threshold. The perception threshold may be representative of the characteristic ECAP value at which patient 105 can perceive the delivery of the corresponding stimulation pulse. If the characteristic ECAP value is not greater than the ECAP parameter threshold ("NO" branch of block 912), processing circuitry 210 increases the level of the next control pulse by a second amount (914). Put another way, if the characteristic ECAP value remains below the perception threshold, processing circuitry 210 may determine that the control pulses currently being delivered by IMD 200 are below the perception threshold. Processing circuitry 210 may increase the level of the control pulses by the second amount such that the process returns to block 910. As such, processing circuitry 210 may iteratively increase the level of stimulation (e.g., an amplitude) by the second amount until the control pulse elicits a characteristic ECAP value that is greater than the perception threshold. The second amount may, in some cases, be significantly less than the first amount. In this manner, when processing circuitry 210 decreases the level of stimulation by the first amount and subsequently increases the level of stimulation by the second amount, the process may perform several iterations of increasing the level of stimulation by the second amount before the stimulation returns to the level that it was at before the start of the process of FIG. 9.

If the characteristic ECAP value is greater than the perception threshold ("YES" branch of block 912), processing circuitry 210 may determine level of the control pulse (e.g., the amplitude) that elicited the characteristic ECAP value that was greater than the perception threshold (916). In some examples, processing circuitry 210 determines that the level of the stimulation delivered prior to the detection of the first characteristic ECAP value that is greater than the perception threshold is the determined level to use to determine the stimulation parameter values. Subsequently, processing circuitry 210 may update therapy stimulation programs 214 based on the level of stimulation that achieved the perception threshold (918). In some examples, processing circuitry 210 sets therapy stimulation programs 214 such that IMD 200 delivers informed pulses with a level (e.g., amplitude) at a fraction of the level of control pulses that achieved the perception threshold. In some examples, the fraction is greater than 0.50 and less than 0.99. For example, if the fraction is 0.75 (or 75 percent of the stimulation level), processing circuitry 210 may determine the informed pulse to have a level, or amplitude, of 4.5 mA if the control pulse of 6 mA resulted in a characteristic ECAP value that achieved the perception threshold.

Figure 10:
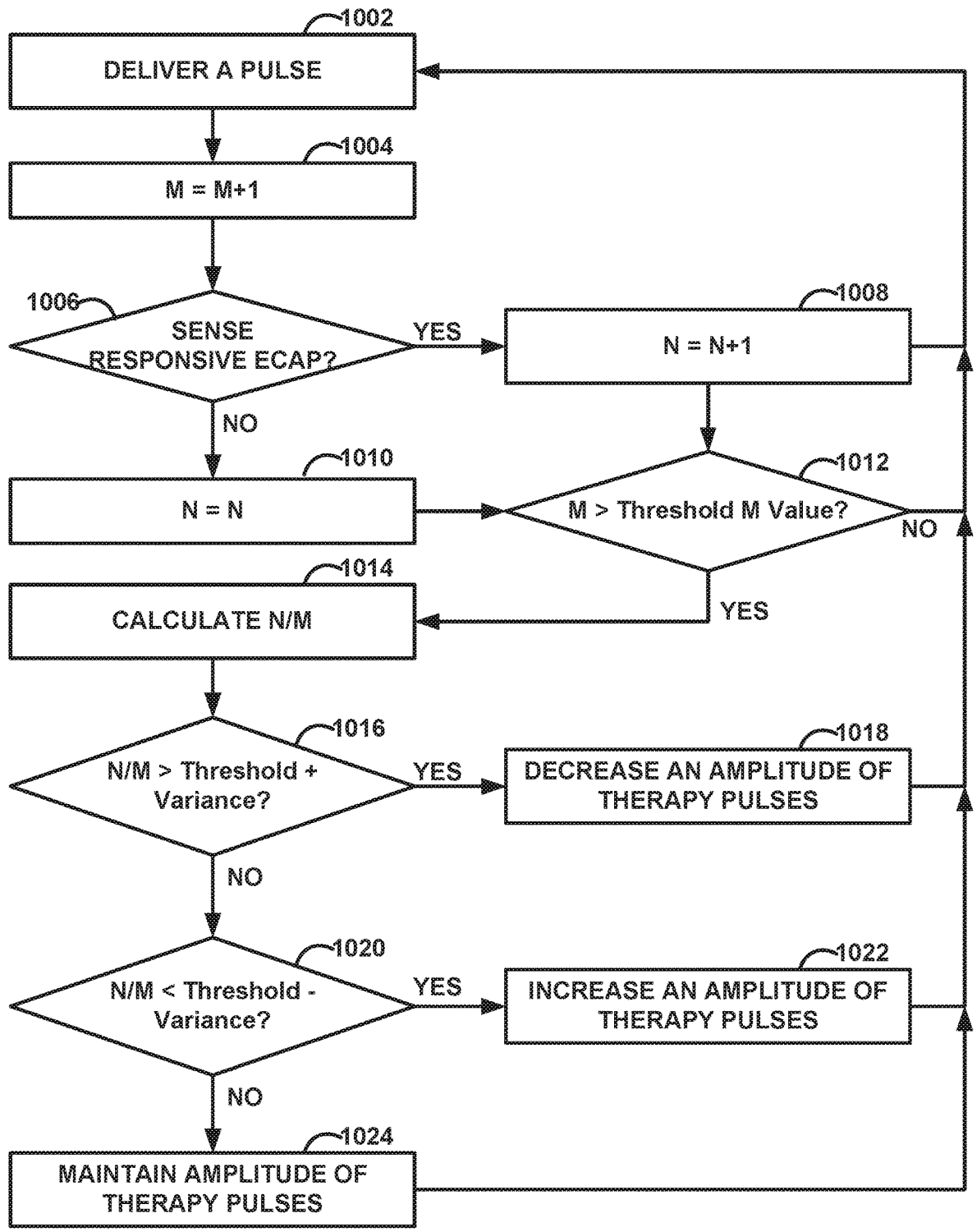
FIG. 10 is a flow diagram illustrating an example operation for determining a stimulation parameter according to a detection threshold, in accordance with one or more techniques of this disclosure.

FIG. 10 is a flow diagram illustrating an example operation for determining stimulation parameter values based on a detection threshold, in accordance with one or more techniques of this disclosure. For convenience, FIG. 10 is described with respect to IMD 200 of FIG. 2. However, the techniques of FIG. 10 may be performed by different components of IMD 200 or by additional or alternative medical devices. FIG. 10 will be described using control pulses for eliciting detectable ECAP signals, where the control pulses may be therapeutic or non-therapeutic to the patient. IMD 200, for example, may use detected ECAP signals to determine one or more parameters of the control pulses, determine one or more parameters of a set of informed pulses, determine one or more parameters of other pulses that do not elicit ECAPs, or any combination thereof.

In the example operation of FIG. 10, IMD 200 delivers a pulse (1002) to a patient (e.g., patient 105 of FIG. 1) via electrodes 232, 234. In some examples, the pulse is a control pulse of the plurality of control pulses delivered by IMD 200 according to ECAP test stimulation programs 216 stored in storage device 212. In other examples, the pulse is an informed pulse of the plurality of informed pulses delivered by IMD 200 according to therapy stimulation programs 214 stored in storage device 212. In examples where the pulse is a control pulse, the control pulse may be interleaved at least partially with informed pulses of the plurality of informed pulses. Based on IMD 200 delivering the pulse, processing circuitry 210 may increase a pulse count (M) by one (processing circuitry 210 performs the operation M=M+1) (1004). As such, IMD 200 maintains the pulse count, which may increase by one every time when IMD 200 delivers another pulse. In some examples, processing circuitry 210 increases the pulse count by one only when IMD 200 delivers a control pulse, when the ECAP signals are sensed only off of the control pulses. In other examples, processing circuitry 210 increases the pulse count by one when IMD 200 delivers either any pulse from which an ECAP signal is sensed and attempted to be detected.

Processing circuitry 210 determines whether sensing circuitry 206 senses a responsive ECAP (1006), the responsive ECAP corresponding to the pulse delivered by IMD 200 in step 1002. Detection of an ECAP may include when processing circuitry 210 can detect a characteristic of the ECAP signal. For example, to determine whether sensing circuitry 206 senses the responsive ECAP, processing circuitry may receive a signal from sensing circuitry 206, the signal representative of electric signals sensed via at least some of electrodes 232, 234. If processing circuitry 210 is able to identify and differentiate a waveform from noise in the signal received from sensing circuitry 206, processing circuitry 210 may identify the waveform as an ECAP responsive to the pulse delivered by IMD 200. Alternatively, in some examples, if processing circuitry 210 is not able to identify and differentiate a waveform from noise in the signal received from sensing circuitry 206, processing circuitry 210 may determine that sensing circuitry 206 did not sense an ECAP responsive to the pulse delivered by IMD 200. In some cases, processing circuitry 210 "looks" for the responsive ECAP in a portion of the signal received by sensing circuitry 206 which occurs over a period of time after IMD 200 delivers the pulse in step 1002. In examples where the pulse is a control pulse, the period of time occurs after IMD 200 delivers the pulse and before IMD 200 delivers a subsequent informed pulse or control pulse. Additionally, in examples where the pulse is an informed pulse, the period of time occurs after IMD 200 delivers the pulse and before IMD 200 delivers a subsequent informed pulse or control pulse.

If IMD 200 senses a responsive ECAP ("YES" branch of block 1006), processing circuitry 210 increases a responsive ECAP count (N) by one (processing circuitry 210 performs the operation N=N+1) (1008). Alternatively, if IMD 200 does not sense a responsive ECAP ("NO" branch of block 1006), processing circuitry 210 maintains the responsive ECAP count (processing circuitry 210 performs the operation N=N) (1010). In this way, the responsive ECAP count represents a running tally of how many pulses delivered by IMD 200 resulted in a responsive ECAP sensed by sensing circuitry 206. At any time, processing circuitry 210 may reset the responsive ECAP count N. In some examples, if processing circuitry 210 resets the responsive ECAP count N, processing circuitry 210 also resets the pulse count M.

After processing circuitry 210 either increases the responsive ECAP count by one or maintains the responsive ECAP count, processing circuitry 210 determines if the pulse count M is greater than a threshold pulse count value (1012). The threshold pulse count value may be stored in storage device 212 as a part of threshold detection parameters 220. In some examples, the threshold pulse count value is greater than 7 and less than 10,000. In any case, the pulse count value may be predetermined and representative of the number of pulses needed to determine whether or not a representative number of ECAPs have been detected. It may be beneficial for processing circuitry 210 to determine if the pulse count is greater than the threshold pulse count value so that IMD 200 determines the stimulation level according to a threshold ratio (e.g., a detection threshold) with a sufficient number of pulses. If processing circuitry 210 determines that the pulse count is not greater than the threshold pulse count value ("NO" branch of block 1012), the operation may return to block 1002 and IMD 200 may deliver an additional pulse. In some examples where the pulse is a control pulse, the additional pulse may also be a control pulse. In some examples where the pulse is an informed pulse, the additional pulse may also be an informed pulse. If processing circuitry 210 determines that the pulse count is greater than the threshold pulse count value ("YES" branch of block 1012), processing circuitry 210 may proceed to calculate a ratio of the responsive ECAP count N to the pulse count M (e.g., calculate N/M) (1014). In this way, processing circuitry 210 calculates a ratio, or a percentage, of pulses delivered by IMD 200 which correspond with a responsive ECAP that is sensed by sensing circuitry 206. The stimulation level, which represents one or more parameters of control pulses delivered by IMD 200, may be determined in part based on the ratio N/M calculated in step 1014.

If processing circuitry 210 determines that the ratio N/M is greater than a sum of a threshold ratio (representative of the perception threshold) and a variance value ("YES" branch of block 1016), processing circuitry 210 may decrease an amplitude of informed pulses delivered to patient 105 by IMD 200 (1018). In some examples, processing circuitry 210 may also decrease the amplitude of the control pulses). The amplitude of the control pulses and the amplitude of the informed pulses may be related by a gain factor in some examples. Subsequently, the operation of FIG. 10 returns to block 1002 and IMD 200 delivers an additional control pulse. The threshold ratio value may represent a ratio of sensed responsive ECAPs to delivered pulses, the threshold ratio value being indicative of the detection threshold in which informed pulses delivered by IMD 200 create an environment in which responsive ECAPs may be detected by sensing circuitry 206. The variance value may represent an error value, where if processing circuitry 210 determines that the ratio N/M is within the error value of the threshold ratio value, processing circuitry 210 may determine that the ratio N/M is "close enough" to the threshold ratio value. In some examples, the threshold ratio value is greater than 0.25 and less than 0.5. Additionally, in some examples, the variance value is greater than or equal to 0 and less than or equal to 0.1. The threshold ratio value and the variance value may be stored in storage device 212 as a part of threshold detection parameters 220.

If processing circuitry 210 determines that the ratio N/M is not greater than the sum of the threshold ratio value and the variance value ("NO" branch of block 1016), processing circuitry 210 determines if the ratio N/M is less than the threshold ratio value minus the variance value (1020). If processing circuitry 210 determines that the ratio N/M is less than the threshold ratio value minus the variance value ("YES" branch of block 1020), processing circuitry 210 increases an amplitude of the informed pulses delivered by IMD 200 to patient 105 (1022), the operation of FIG. 10 returns to block 1002, and IMD 200 delivers an additional pulse. In some examples where the pulse is a control pulse, the additional pulse is also a control pulse. In some examples where the pulse is an informed pulse, the additional pulse is also an informed pulse. If processing circuitry 210 determines that the ratio N/M is not less than the threshold ratio value minus the variance value ("NO" branch of block 1020), processing circuitry 210 maintains the amplitude of the informed pulses (1024) and continues to deliver additional pulses (1002). An upper-bound of the threshold ratio value window is given by the sum of a threshold ratio value and a variance value, and a lower-bound of the threshold ratio value window is given by the threshold ratio value minus the variance value.

As discussed above, the amplitude of the informed pulses may be set to be a fraction of stimulation level at which pulses elicited detectable ECAPs at the threshold ratio. In some examples, the stimulation level may be the amplitude of control pulses that elicited the detected ECAP signals. For example, the fraction may be greater than 0.50 and less than 0.99.

Although the operation of FIG. 10 is described for adjusting the amplitude of the informed pulses, other parameter values may be changed in other examples. For example, sensed ECAP signals may be used to increase or decrease the pulse width of the informed pulse to adjust the amount of charge delivered to the tissue to maintain consistent volume of neural activation. In other examples, electrode combinations may be adjusted in order to deliver different amounts of charge and modify the number of neurons being recruited by each informed pulse. In other examples, processing circuitry 210 may be configured to adjust a slew rate of the informed pulses (i.e., the rate of change of the voltage and/or amplitude at the beginning and/or end of the pulse or each phase of the pulse) in response to the ratio N/M being greater than or less than the threshold ratio value window. For example, if the representative amplitude of the ECAP signal is greater than the upper-bound of the threshold ratio value window, processing circuitry 210 may decrease the slew rate of the next informed pulses (i.e., ramp up the amplitude of the pulse more slowly). If the representative amplitude of the ECAP signal is lower than the lower-bound of the threshold ratio value window, processing circuitry 210 may increase the slew rate of the next informed pulses (i.e., ramp up the amplitude of the pulse more quickly). The slew rate may contribute to the intensity of the pulse. Processing circuitry 210 may change one or more parameters defining the informed pulse according to the operation of FIG. 10.

The following examples are example systems, devices, and methods described herein.

Example 1: A medical device comprising: stimulation generation circuitry configured to deliver electrical stimulation therapy to a patient, wherein the electrical stimulation therapy comprises a plurality of therapy pulses; sensing circuitry configured to sense one or more evoked compound action potential (ECAP) signals, wherein the sensing circuitry is configured to sense each ECAP signal of the one or more ECAPs elicited by a respective control pulse of a plurality of control pulses; and processing circuitry configured to: determine, based on the one or more ECAP signals, a stimulation level for the plurality of control pulses that achieves a stimulation threshold; determine, based on the stimulation level, a value of a stimulation parameter that at least partially defines the plurality of therapy pulses of the electrical stimulation therapy; and control the stimulation generation circuitry to deliver the electrical stimulation therapy to the patient according to the value of the stimulation parameter.

Example 2: The medical device of example 1, wherein the plurality of therapy pulses comprises a plurality of informed pulses, and wherein at least some of the plurality of informed pulses are interleaved with at least some control pulses of the plurality of control pulses.

Example 3: The medical device of example 2, wherein the processing circuitry is configured to determine the value of the stimulation parameter by applying a fraction value to the stimulation level to determine the value of the stimulation parameter that at least partially defines the plurality of informed pulses.

Example 4: The medical device of any of examples 2-3, wherein the processing circuitry is configured to determine the value of the stimulation parameter to be less than 100 percent of the stimulation level.

Example 5: The medical device of example 4, wherein the value of the stimulation parameter is determined from a range of approximately 40 percent to approximately 99 percent of the stimulation level.

Example 6: The medical device of any of examples 2-5, wherein the stimulation level and the stimulation parameter are respective current amplitudes.

Example 7: The medical device of any of examples 1-6, wherein to determine the stimulation level, the processing circuitry is configured to: control the stimulation circuitry to deliver a set of control pulses, from the plurality of control pulses, having an iteratively increasing value of a stimulation parameter that at least partially defines respective control pulses from the set of control pulses; and determine the stimulation level to be the value of the stimulation parameter that at least partially defined the control pulse from the set of control pulses that results in a characteristic of the ECAP signal that achieved the stimulation threshold.

Example 8: The medical device of example 7, wherein the characteristic of the ECAP signal comprises at least one of a peak current amplitude, a peak voltage amplitude, a gradient, or an area under at least one peak of the ECAP signal.

Example 9: The medical device of any of examples 1-8, wherein the stimulation threshold is a perception threshold associated with a characteristic of the ECAP signal that indicates the patient is capable of perceiving the control pulses.

Example 10: The medical device of any of examples 1-9, wherein the stimulation threshold is a detection threshold associated with a characteristic of the ECAP signal detectable from a delivered control pulse.

Example 11: The medical device of example 10, wherein the processing circuitry is configured to determine the stimulation level to be a value of a stimulation parameter at which a threshold ratio of a number of times the respective ECAP signals are detected for a set of consecutive control pulses of the plurality of control pulses.

Example 12: The medical device of example 11, wherein the set of consecutive control pulses comprises a first set of consecutive control pulses, the value of the stimulation parameter is a first value of the stimulation parameter, and the number of times the respective ECAP signals were detected is a first number of times the respective ECAP signals were detected, and wherein the processing circuitry is configured to: determine, from a second set of consecutive control pulses of the plurality of control pulses at least partially defined by the first value of the stimulation parameter, a second number of times the respective ECAP signals were detected; determine a ratio of the second number of times the respective ECAP signal was detected to a number of pulses in the second set of consecutive control pulses; determine that the ratio is one of greater than the threshold ratio or less than the threshold ratio; responsive to determining that the ratio is greater than the threshold ratio, select a decreased value of the stimulation parameter for subsequent therapy pulses; and responsive to determining that the ratio is less than the threshold ratio, select an increased value of the stimulation parameter for the subsequent therapy pulses.

Example 13: The medical device of example 12, wherein the threshold ratio value is greater than 0.25 and less than 0.75.

Example 14: The medical device of any of examples 1-13, wherein the plurality of therapy pulses comprises the plurality of control pulses.

Example 15: The medical device of any of examples 1-14, wherein the medical device is an implantable medical device.

Example 16: A method comprising: delivering, by stimulation generation circuitry, electrical stimulation therapy to a patient, wherein the electrical stimulation therapy comprises a plurality of therapy pulses; sensing, by sensing circuitry, one or more evoked compound action potential (ECAP) signals, wherein the sensing circuitry is configured to sense each ECAP signal of the one or more ECAPs elicited by a respective control pulse of a plurality of control pulses; determining, by processing circuitry and based on the one or more ECAP signals, a stimulation level for the plurality of control pulses that achieves a stimulation threshold; determining, by the processing circuitry and based on the stimulation level, a value of a stimulation parameter that at least partially defines the plurality of therapy pulses of the electrical stimulation therapy; and controlling, by the processing circuitry, the stimulation generation circuitry of to deliver the electrical stimulation therapy to the patient according to the value of the stimulation parameter.

Example 17: The method of example 16, wherein the plurality of therapy pulses comprises a plurality of informed pulses, and wherein delivering the electrical stimulation therapy comprises delivering at least some of the plurality of informed pulses interleaved with at least some control pulses of the plurality of control pulses.

Example 18: The method of example 17, wherein determining the value of the stimulation parameter comprises applying a fraction value to the stimulation level to determine the value of the stimulation parameter that at least partially defines the plurality of informed pulses.

Example 19: The method of any of examples 17-18, wherein determining the value of the stimulation parameter comprises determining the value of the stimulation parameter to be less than 100 percent of the stimulation level.

Example 20: The method of example 19, wherein the value of the stimulation parameter is determined from a range of approximately 40 percent to approximately 99 percent of the stimulation level.

Example 21: The method of any of examples 17-20, wherein the stimulation level and the stimulation parameter are respective current amplitudes.

Example 22: The method of any of examples 16-21, wherein determining the stimulation level comprises: controlling the stimulation circuitry to deliver a set of control pulses, from the plurality of control pulses, having an iteratively increasing value of a stimulation parameter that at least partially defines respective control pulses from the set of control pulses; and determining the stimulation level to be the value of the stimulation parameter that at least partially defined the control pulse from the set of control pulses that results in a characteristic of the ECAP signal that achieved the stimulation threshold.

Example 23: The method of any of examples 16-22, wherein the stimulation threshold is a perception threshold associated with a characteristic of the ECAP signal that indicates the patient is capable of perceiving the control pulses.

Example 24: The method of any of examples 16-23, wherein the stimulation threshold is a detection threshold associated with a characteristic of the ECAP signal detectable from a delivered control pulse.

Example 25: The method of example 24, wherein determining the stimulation level comprises determining the stimulation level to be a value of a stimulation parameter at which a threshold ratio of a number of times the respective ECAP signals are detected for a set of consecutive control pulses of the plurality of control pulses.

Example 26: The method of example 25, wherein the set of consecutive control pulses comprises a first set of consecutive control pulses, the value of the stimulation parameter is a first value of the stimulation parameter, and the number of times the respective ECAP signals were detected is a first number of times the respective ECAP signals were detected, and wherein the method further comprises: determining, by the processing circuitry and from a second set of consecutive control pulses of the plurality of control pulses at least partially defined by the first value of the stimulation parameter, a second number of times the respective ECAP signals were detected; determining, by the processing circuitry, a ratio of the second number of times the respective ECAP signal was detected to a number of pulses in the second set of consecutive control pulses; determining, by the processing circuitry, that the ratio is one of greater than the threshold ratio or less than the threshold ratio; responsive to determining that the ratio is greater than the threshold ratio, selecting, by the processing circuitry, a decreased value of the stimulation parameter for subsequent informed pulses; and responsive to determining that the ratio is less than the threshold ratio, selecting, by the processing circuitry, an increased value of the stimulation parameter for the subsequent informed pulses.

Example 27: The method of example 26, wherein the threshold ratio value is greater than 0.25 and less than 0.75.

Example 28: The method of any of examples 26-27, wherein an implantable medical device comprises the stimulation generation circuitry, the sensing circuitry, and the processing circuitry.

Example 29: A computer-readable medium comprising instructions that, when executed by a processor, causes the processor to: control stimulation generation circuitry to deliver electrical stimulation therapy to a patient, wherein the electrical stimulation therapy comprises a plurality of therapy pulses; control sensing circuitry to sense one or more evoked compound action potential (ECAP) signals, wherein the sensing circuitry is configured to sense each ECAP signal of the one or more ECAPs elicited by a respective control pulse of a plurality of control pulses; determine, based on the one or more ECAP signals, a stimulation level for the plurality of control pulses that achieves a stimulation threshold; determine, based on the stimulation level, a value of a stimulation parameter that at least partially defines the plurality of therapy pulses of the electrical stimulation therapy; and control the stimulation generation circuitry to deliver the electrical stimulation therapy to the patient according to the value of the stimulation parameter.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A medical device comprising:
   stimulation generation circuitry configured to deliver electrical stimulation therapy to a patient, wherein the electrical stimulation therapy comprises a plurality of therapy pulses, and wherein the stimulation generation circuitry is configured to deliver a plurality of control pulses at least partially interleaved with the plurality of therapy pulses;
   sensing circuitry configured to sense evoked compound action potential (ECAP) signals elicited by the plurality of control pulses instead of the plurality of therapy pulses, wherein the plurality of control pulses are different than the plurality of therapy pulses; and
   processing circuitry configured to:
      determine, based on at least one ECAP signal of the ECAP signals, a stimulation level for the plurality of control pulses that achieves a stimulation threshold;
      determine, based on the stimulation level, a value of a stimulation parameter that at least partially defines the plurality of therapy pulses of the electrical stimulation therapy; and
      control the stimulation generation circuitry to deliver the electrical stimulation therapy to the patient according to the value of the stimulation parameter.

2. The medical device of claim 1, wherein the plurality of therapy pulses comprises a plurality of informed pulses.

3. The medical device of claim 2, wherein the processing circuitry is configured to determine the value of the stimulation parameter by applying a fraction value to the stimulation level to determine the value of the stimulation parameter that at least partially defines the plurality of informed pulses.

4. The medical device of claim 2, wherein the processing circuitry is configured to determine the value of the stimulation parameter to be less than 100 percent of the stimulation level.

5. The medical device of claim 4, wherein the value of the stimulation parameter is determined from a range of 40 percent to 99 percent of the stimulation level.

6. The medical device of claim 2, wherein the stimulation level and the stimulation parameter are respective current amplitudes.

7. The medical device of claim 1, wherein to determine the stimulation level, the processing circuitry is configured to:
   control the stimulation circuitry to deliver a set of control pulses, from the plurality of control pulses, having an iteratively increasing value of a stimulation parameter that at least partially defines respective control pulses from the set of control pulses; and
   determine the stimulation level to be the value of the stimulation parameter that at least partially defined the control pulse from the set of control pulses that results in a characteristic of the ECAP signal that achieved the stimulation threshold.

8. The medical device of claim 7, wherein the characteristic of the ECAP signal comprises at least one of a peak current amplitude, a peak voltage amplitude, a gradient, or an area under at least one peak of the ECAP signal.

9. The medical device of claim 1, wherein the stimulation threshold is a perception threshold associated with a characteristic of the ECAP signal that indicates the patient is capable of perceiving the control pulses.

10. The medical device of claim 1, wherein the stimulation threshold is a detection threshold associated with a characteristic of the ECAP signal detectable from a delivered control pulse.

11. The medical device of claim 10, wherein the processing circuitry is configured to determine the stimulation level to be a value of a stimulation parameter at which a threshold ratio of a number of times the respective ECAP signals are detected for a set of consecutive control pulses of the plurality of control pulses.

12. The medical device of claim 11, wherein the set of consecutive control pulses comprises a first set of consecutive control pulses, the value of the stimulation parameter is a first value of the stimulation parameter, and the number of times the respective ECAP signals were detected is a first number of times the respective ECAP signals were detected, and wherein the processing circuitry is configured to:
   determine, from a second set of consecutive control pulses of the plurality of control pulses at least partially defined by the first value of the stimulation parameter, a second number of times the respective ECAP signals were detected;
   determine a ratio of the second number of times the respective ECAP signal was detected to a number of pulses in the second set of consecutive control pulses;
   determine that the ratio is one of greater than the threshold ratio or less than the threshold ratio;
   responsive to determining that the ratio is greater than the threshold ratio, select a decreased value of the stimulation parameter for subsequent therapy pulses; and
   responsive to determining that the ratio is less than the threshold ratio, select an increased value of the stimulation parameter for the subsequent therapy pulses.

13. The medical device of claim 12, wherein the threshold ratio value is greater than 0.25 and less than 0.75.

14. The medical device of claim 1, wherein the medical device is an implantable medical device.

15. A method comprising:
   delivering, by stimulation generation circuitry, electrical stimulation therapy to a patient, wherein the electrical stimulation therapy comprises a plurality of therapy pulses;
   delivering, by the stimulation generation circuitry, a plurality of control pulses at least partially interleaved with the plurality of therapy pulses;
   sensing, by sensing circuitry, one or more evoked compound action potential (ECAP) signals elicited by a control pulse of the plurality of control pulses instead of the plurality of therapy pulses, wherein the plurality of control pulses are different than the plurality of therapy pulses;

determining, by processing circuitry and based on at least one ECAP signal of the ECAP signals, a stimulation level for the plurality of control pulses that achieves a stimulation threshold;

determining, by the processing circuity and based on the stimulation level, a value of a stimulation parameter that at least partially defines the plurality of therapy pulses of the electrical stimulation therapy; and controlling, by the processing circuitry, the stimulation generation circuitry of to deliver the electrical stimulation therapy to the patient according to the value of the stimulation parameter.

16. The method of claim 15, wherein the plurality of therapy pulses comprises a plurality of informed pulses.

17. The method of claim 16, wherein determining the value of the stimulation parameter comprises applying a fraction value to the stimulation level to determine the value of the stimulation parameter that at least partially defines the plurality of informed pulses.

18. The method of claim 16, wherein determining the value of the stimulation parameter comprises determining the value of the stimulation parameter to be less than 100 percent of the stimulation level.

19. The method of claim 18, wherein the value of the stimulation parameter is determined from a range of 40 percent to 99 percent of the stimulation level.

20. The method of claim 16, wherein the stimulation level and the stimulation parameter are respective current amplitudes.

21. The method of claim 15, wherein determining the stimulation level comprises:
controlling the stimulation circuitry to deliver a set of control pulses, from the plurality of control pulses, having an iteratively increasing value of a stimulation parameter that at least partially defines respective control pulses from the set of control pulses; and
determining the stimulation level to be the value of the stimulation parameter that at least partially defined the control pulse from the set of control pulses that results in a characteristic of the ECAP signal that achieved the stimulation threshold.

22. The method of claim 15, wherein the stimulation threshold is a perception threshold associated with a characteristic of the ECAP signal that indicates the patient is capable of perceiving the control pulses.

23. The method of claim 15, wherein the stimulation threshold is a detection threshold associated with a characteristic of the ECAP signal detectable from a delivered control pulse.

24. The method of claim 23, wherein determining the stimulation level comprises determining the stimulation level to be a value of a stimulation parameter at which a threshold ratio of a number of times the respective ECAP signals are detected for a set of consecutive control pulses of the plurality of control pulses.

25. The method of claim 24, wherein the set of consecutive control pulses comprises a first set of consecutive control pulses, the value of the stimulation parameter is a first value of the stimulation parameter, and the number of times the respective ECAP signals were detected is a first number of times the respective ECAP signals were detected, and wherein the method further comprises:
determining, by the processing circuitry and from a second set of consecutive control pulses of the plurality of control pulses at least partially defined by the first value of the stimulation parameter, a second number of times the respective ECAP signals were detected;
determining, by the processing circuitry, a ratio of the second number of times the respective ECAP signal was detected to a number of pulses in the second set of consecutive control pulses;
determining, by the processing circuitry, that the ratio is one of greater than the threshold ratio or less than the threshold ratio;
responsive to determining that the ratio is greater than the threshold ratio, selecting, by the processing circuitry, a decreased value of the stimulation parameter for subsequent informed pulses; and
responsive to determining that the ratio is less than the threshold ratio, selecting, by the processing circuitry, an increased value of the stimulation parameter for the subsequent informed pulses.

26. The method of claim 25, wherein the threshold ratio value is greater than 0.25 and less than 0.75.

27. The method of claim 25, wherein an implantable medical device comprises the stimulation generation circuitry, the sensing circuitry, and the processing circuitry.

28. A non-transitory computer-readable medium comprising instructions that, when executed by a processor, causes the processor to:
control stimulation generation circuitry to deliver electrical stimulation therapy to a patient, wherein the electrical stimulation therapy comprises a plurality of therapy pulses;
control the stimulation generation circuitry to deliver a plurality of control pulses at least partially interleaved with the plurality of therapy pulses;
control sensing circuitry to sense evoked compound action potential (ECAP) signals elicited by the plurality of control pulses instead of the plurality of therapy pulses, wherein the plurality of control pulses are different than the plurality of therapy pulses;
determine, based on at least one ECAP signal of the ECAP signals, a stimulation level for the plurality of control pulses that achieves a stimulation threshold;
determine, based on the stimulation level, a value of a stimulation parameter that at least partially defines the plurality of therapy pulses of the electrical stimulation therapy; and
control the stimulation generation circuitry to deliver the electrical stimulation therapy to the patient according to the value of the stimulation parameter.

* * * * *